(12) United States Patent
Sackellares et al.

(10) Patent No.: US 10,893,821 B2
(45) Date of Patent: Jan. 19, 2021

(54) ELECTRODE ASSEMBLIES AND ELECTROENCEPHALOGRAPHIC DEVICES, METHODS AND KITS

(71) Applicant: EncephaloDynamics, Inc., Gainesville, FL (US)

(72) Inventors: James Chris Sackellares, Gainesville, FL (US); Scott Bearden, Waldo, FL (US); Micah Streiff, Decatur, GA (US)

(73) Assignee: EncephaloDynamics, Inc., Gainesville, FL (US)

( * ) Notice: Subject to any disclaimer, the term of this patent is extended or adjusted under 35 U.S.C. 154(b) by 307 days.

(21) Appl. No.: 15/994,805

(22) Filed: May 31, 2018

(65) Prior Publication Data

US 2018/0338697 A1 Nov. 29, 2018

Related U.S. Application Data

(63) Continuation-in-part of application No. 14/776,480, filed as application No. PCT/US2014/027804 on Mar. 14, 2014, now abandoned.

(Continued)

(51) Int. Cl.
*A61B 5/0478* (2006.01)
*A61B 5/0402* (2006.01)
(Continued)

(52) U.S. Cl.
CPC .......... *A61B 5/0478* (2013.01); *A61B 5/0408* (2013.01); *A61B 5/04026* (2013.01); *A61B 5/0476* (2013.01); *A61B 5/6803* (2013.01); *A61B 5/6814* (2013.01); *A61B 5/6843* (2013.01); *A61B 5/7232* (2013.01);
(Continued)

(58) Field of Classification Search
CPC .................. A61B 5/0478; A61B 2562/168
See application file for complete search history.

(56) References Cited

U.S. PATENT DOCUMENTS 3,998,213 A 12/1976 Price
4,033,334 A 7/1977 Fletcher et al.
(Continued)

FOREIGN PATENT DOCUMENTS

EP 2561806 A1 2/2013
JP S57160438 A 10/1982
(Continued)

OTHER PUBLICATIONS

International Search Report for PCT/US2014/027804 dated Aug. 1, 2014.
(Continued)

*Primary Examiner* — Lee S Cohen
(74) *Attorney, Agent, or Firm* — Locke Lord LLP; Daniel J. Fiorello

(57) ABSTRACT

In accordance with at least one aspect of this disclosure, an encephalographic electrode assembly can include a wicking element that has a wick body, one or more long legs extending from the wick body and inserted into the one or more hollow contact probes, and one or more short legs, which are shorter than the long legs, extending from the wick body and inserted into the one or more short reservoir sleeves. The short legs are configured to prevent slide-out of the wicking element from the reservoir body.

20 Claims, 20 Drawing Sheets

Related U.S. Application Data

(60) Provisional application No. 61/783,302, filed on Mar. 14, 2013.

(51) Int. Cl.
*A61B 5/0408* (2006.01)
*A61B 5/00* (2006.01)
*A61B 5/0476* (2006.01)

(52) U.S. Cl.
CPC . *A61B 2562/0215* (2017.08); *A61B 2562/046* (2013.01); *A61B 2562/125* (2013.01); *A61B 2562/164* (2013.01); *A61B 2562/168* (2013.01); *A61B 2562/182* (2013.01)

(56) References Cited

U.S. PATENT DOCUMENTS

| | | | |
|---|---|---|---|
| 5,038,782 | A | 8/1991 | Gevins et al. |
| 6,067,464 | A | 5/2000 | Musha |
| 7,551,952 | B2 | 6/2009 | Gevins et al. |
| 8,131,381 | B1 | 3/2012 | Santjer |
| 8,457,709 | B2 | 6/2013 | Matthews et al. |
| 8,774,890 | B2 | 7/2014 | Ready et al. |
| 2002/0177767 | A1 | 11/2002 | Burton et al. |
| 2007/0004978 | A1 | 1/2007 | Ponton |
| 2008/0027345 | A1 | 1/2008 | Kumada et al. |
| 2009/0099423 | A1 | 4/2009 | Al-Ali et al. |
| 2009/0099473 | A1 | 4/2009 | Dunseath et al. |
| 2010/0198042 | A1 | 8/2010 | Popescu et al. |
| 2011/0015503 | A1 | 1/2011 | Joffe et al. |
| 2011/0315548 | A1 | 12/2011 | Yamashita |
| 2012/0136233 | A1 | 5/2012 | Yamashita |
| 2012/0143020 | A1 | 6/2012 | Bordoley et al. |
| 2012/0238890 | A1 | 9/2012 | Baker et al. |
| 2016/0022981 | A1* | 1/2016 | Wingeier .............. A61B 5/0478 607/139 |
| 2017/0065816 | A1 | 3/2017 | Wingeier et al. |

FOREIGN PATENT DOCUMENTS

| | | |
|---|---|---|
| JP | H03-003304 U | 1/1991 |
| JP | H10165386 A | 6/1998 |
| JP | 2006006666 A | 1/2006 |
| JP | 2012005777 A | 1/2012 |
| WO | WO-03/087851 A2 | 10/2003 |
| WO | WO-2011132756 A1 | 10/2011 |

OTHER PUBLICATIONS

PCT International Preliminary Report on Patentability and Written Opinion dated Sep. 15, 2015 and Aug. 1, 2014, issued in corresponding PCT International Patent Application No. PCT/US2014/027804.

Office Action, of the Japan Patent Office, dated Mar. 6, 2018 in corresponding Japanese Patent Application No. 2016-502629.

Extended European Search Report, of the European Patent Office, dated Oct. 7, 2016, issued in corresponding European Patent Application No. 14768823.8.

International Search Report and Written Opinion issued in corresponding PCT Patent Application No. PCT/US2019/034748 dated Sep. 18, 2019.

* cited by examiner

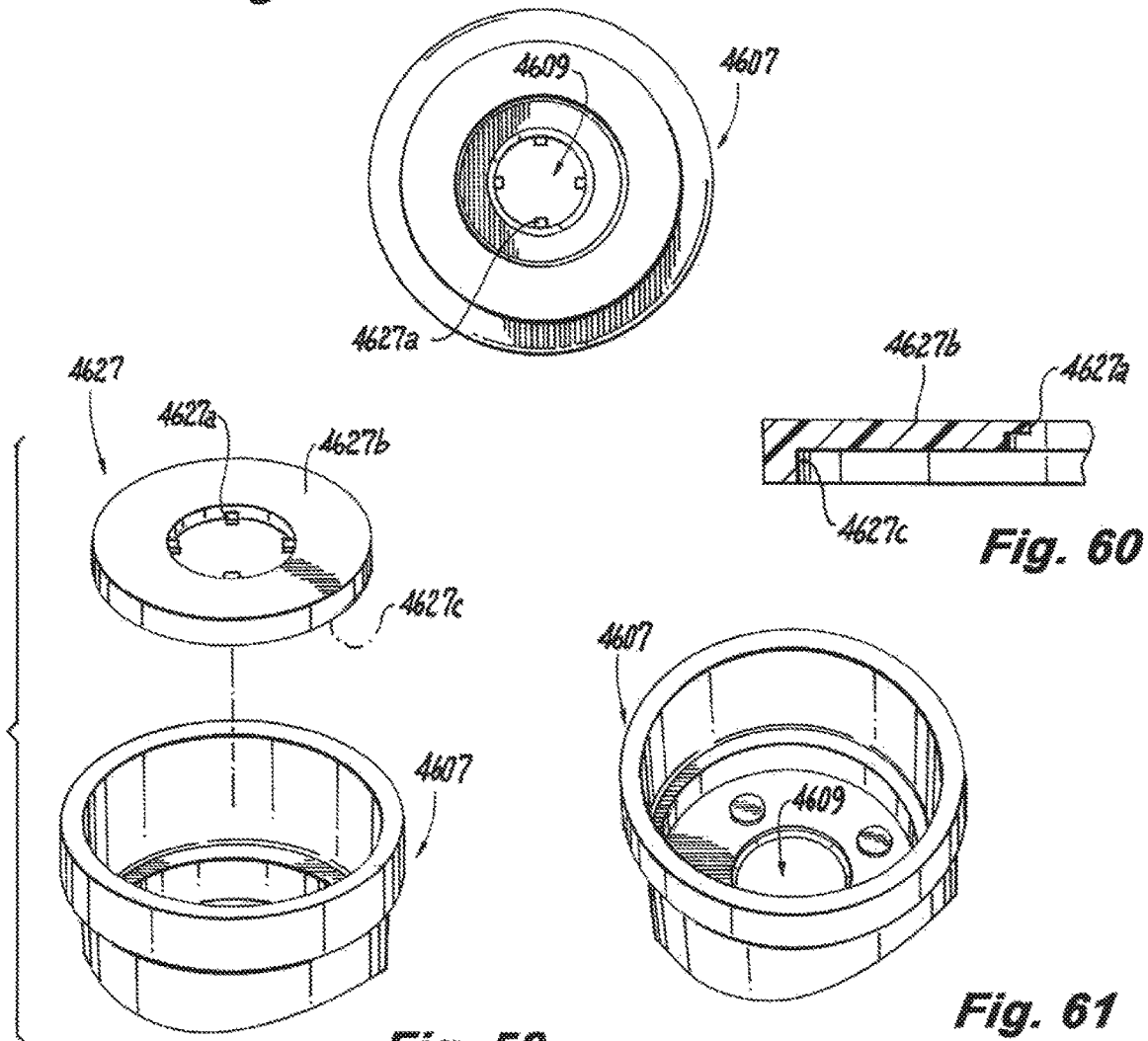
Fig. 57
Fig. 60
Fig. 61
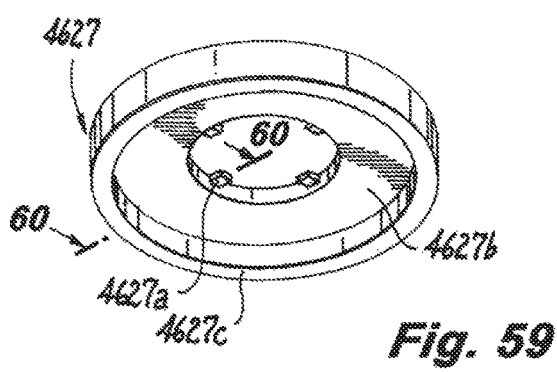
Fig. 58
Fig. 59
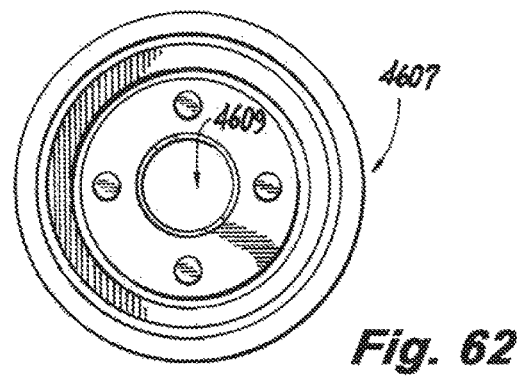
Fig. 62

ELECTRODE ASSEMBLIES AND ELECTROENCEPHALOGRAPHIC DEVICES, METHODS AND KITS

CROSS-REFERENCE TO RELATED APPLICATIONS

This application is a continuation-in-part of U.S. Non-Provisional patent application Ser. No. 14/776,480, filed Sep. 14, 2015, now abandoned, which is a National Stage Entry of International (PCT) Patent Application No. PCT/US2014/027804, filed Mar. 14, 2014, which claims the benefit of and priority to Provisional Patent Application No. 61/783,302, filed Mar. 14, 2013, the entire contents of each being incorporated by reference herein.

FIELD

This disclosure related to electrode assemblies, more specifically to electrode assemblies that can be used with electroencephalography.

BACKGROUND

Electroelectroencephalography is a technology for measuring the voltage and frequency of electrical activity from neurons in the cerebral cortex. Electroencephalogram (EEG) electrodes can record brainwaves using electrodes attached to the scalp, placed on the surface of the brain (subdural electrodes), or within brain tissue (depth electrodes).

A scalp EEG is a non-invasive procedure that provides useful information about brain state and function. This methodology is used in many fields of neuroscience (e.g., psychology, epilepsy, brain machine interface, and sleep research) for recording and analyzing brain state and function. It is used widely as a diagnostic tool in clinical neurology to evaluate and monitor brain function and to identify disturbances in the function of the brain caused by a variety of insults to the brain such as concussion, traumatic injury, stroke, tumor, encephalopathies due to toxins or metabolic disturbances, and seizures. Many disturbances of brain function can be identified by analysis of brief multi-channel EEG recordings using electrodes placed in specific locations on the scalp based off reference anatomical landmarks. The most widely accepted system of electrode placement is the International 10/20 System of electrode placement.

SUMMARY

At least one aspect of this disclosure provides an electrode assembly including a reservoir defining a plurality of openings on a first surface of the reservoir, a wicking material extending through one or more of the plurality of openings, and a conductive terminal.

This aspect of this disclosure can have a variety of embodiments. The wicking material can be porous. The wicking material can include felt and/or foam and/or any other suitable absorptive material.

The electrode assembly can include a conductive fluid absorbed within the wicking material and in contact with the conductive terminal. In some embodiments, the conductive fluid can be saline.

The conductive terminal can be spring-loaded and apply pressure to the conductive fluid. The reservoir can be fabricated from a deformable material such that reservoir deforms when pressed against skin and creates elevated fluid pressure within the reservoir. In some embodiments, the first surface can be substantially flat.

Each of the plurality of openings can be each formed on an end of one of a plurality of probes. The plurality of probes can have a height of about 8 mm. The plurality of probes can have a height selected from the group including between about 1 mm and about 2 mm, between about 2 mm and about 3 mm, between about 3 mm and about 4 mm, between about 4 mm and about 5 mm, between about 5 mm and about 6 mm, between about 6 mm and about 7 mm, between about 7 mm and about 8 mm, and between about 8 mm and about 9 mm, or any other suitable height. The plurality of probes can have an external diameter of about 3 mm or any other suitable diameter. In some embodiments, the plurality of probes can have an external diameter selected between about 2 mm and about 4 mm or any other suitable diameter. The plurality of probes can have an internal diameter of about 2 mm or any other suitable diameter.

In some embodiments, the reservoir can define between 5 and 20 openings. In some embodiments, the reservoir can define between 5 and 10 openings.

In some embodiments, the wicking material can extend about 3 mm beyond the plurality of openings. The conductive terminal can be located on an opposite side of the plurality of openings. The conductive terminal can be a silver/silver chloride electrode.

Another aspect of this disclosure provides a device to record brain waves including a headpiece (e.g., an elastic cap, rigid helmet, hat, or other suitable headpiece) adapted and configured for placement on a subject's head, a plurality of electrode assemblies as described herein arranged on an interior surface of the headpiece, and one or more connector cables adapted and configured for coupling with the plurality of electrode assemblies.

This aspect of this disclosure can have a variety of embodiments. The plurality of electrode assemblies can include a plurality of electrode assemblies as described herein located in positions corresponding to regions where the subject does not have hair, and a plurality of electrodes assemblies as described herein located in positions corresponding to regions where the subject does have hair.

In some embodiments, the plurality electrode of assemblies can be located within the headpiece at locations corresponding to the 10-20 System or in any other suitable arrangement. Each of the electrode assemblies can include a mushroom-shaped extension of the conductive terminal that is adapted and configured to snap into one of a plurality of ring-shaped receptacles located on the cap at the locations corresponding to the 10-20 System.

The encephalographic device can include a recording device adapted and configured for coupling with the one or more connector cables and recording electrical signals received from the plurality of electrode symbols via the one or more connector cables.

In some embodiments, the one or more connector cables can be overmolded into the headpiece. The one or more connector cables can include metal wire conductors and conductive cloth.

Another aspect of this disclosure provides an electroencephalographic method including, placing the electroencephalographic recording device as described herein on a subject's head; and recording electrical signals received from the plurality of electrode symbols via the one or more connector cables.

This aspect of this disclosure can have a variety of embodiments. The method can include applying a conductive fluid to the wicking material. The method can include removing a seal from the electrode assemblies. The method can include presenting the electrical signals to a medical professional and/or receiving the electrical signals at a recording and/or monitoring instrument configured to generate a visual tracing of the electrical signals from the various electrodes for interpretation by a user.

Another aspect of this disclosure provides an electroencephalography kit including the encephalographic device as disclosed herein and instructions for use.

In another aspect of this disclosure, an electrode assembly can include a reservoir cap, a reservoir bottom configured to fit to the reservoir cap and define a reservoir therewith, an electrode disposed within the reservoir, and a wicking element in electrical communication with the electrode and configured to absorb a fluid, wherein at least a portion the wicking element is configured to protrude from the reservoir bottom. The wicking element can include a base portion and an array of legs extending therefrom. The wicking element can include a rigid or semi-rigid frame and is coated with a wicking material.

In accordance with at least one aspect of this disclosure, an encephalographic electrode assembly can include a reservoir body defining at least a portion of a reservoir, one or more hollow contact probes extending from the reservoir body, each defining a long leg channel therein that fluidly communicates with the reservoir, one or more short reservoir sleeves extending from the reservoir and defining a short leg channel therein that fluidly communicates with the reservoir, and a wicking element disposed in the reservoir body in fluid communication with the reservoir. The wicking element can include a wick body, one or more long legs extending from the wick body and inserted into the one or more hollow contact probes, and one or more short legs, which are shorter than the long legs, extending from the wick body and inserted into the one or more short reservoir sleeves. The short legs are configured to prevent slide-out of the wicking element from the reservoir body.

The one or more short legs can be larger than the one or more short reservoir sleeves such that an interaction fit is created when the short legs are inserted into the short reservoir sleeves. The one or more short legs can have the same width as the long legs.

The one or more short leg channels can have a smaller width than the one or more long leg channels. The one or more short legs can include at least three short legs positioned to form corners of a triangle.

The one or more short legs or the one or more long legs can include a standoff lip at a base of one or more of the short legs or long legs. Each standoff lip can be configured to provide a space between the reservoir body and the wick body within the reservoir when fully seated against an inner bottom surface of the reservoir body. In certain embodiments, each short leg can include a standoff lip at the base thereof.

Each long leg can be dimensioned such that a tip of each long leg extends beyond a respective hollow contact probe when inserted therein. In certain embodiments, each short leg can be dimensioned to not extend beyond a respective short reservoir sleeve when inserted therein.

The reservoir body can further comprise a probe cover ridge defined on an outer surface thereof and configured to mate with a pocket of a probe cover to retain the probe cover thereto. The reservoir body can include a clip ridge proximal the probe cover ridge and configured to allow a probe clip to attach to the reservoir body to retain the assembly to an elastic cap.

The assembly can further include a reservoir cap sealed to the reservoir body to enclose and/or partially define the reservoir. In certain embodiments, the reservoir cap can be made of hard plastic, and the reservoir body and hollow contact probes can made of an elastic flexible material.

The assembly can include a stabilizer removably attached to the reservoir body. In certain embodiments, the stabilizer can include a ring and a plurality of stabilizer legs radially outward of the hollow contact probes and extending from the ring. The stabilizer can be made of hard plastic and the ring can be interference fit to the reservoir body. In certain embodiments, the stabilizer legs can include rounded droplet tips. In certain embodiments, the stabilizer legs can be angled to extend radially outward from the ring.

The assembly can include a grommet seal disposed in the reservoir cap and configured to allow an electrode wire to pass through the grommet seal to electrically connect to an electrode within the reservoir. The grommet seal can be made of an elastic material.

The grommet seal can include a conical tip and a groove configured to be inserted through a hole in the reservoir cap. In certain embodiments, the grommet seal can include a flange that abuts the reservoir cap (e.g., and can be sealed to the cap with a sealant).

In certain embodiments, the assembly can include an absorptive material disposed within the reservoir and in contact with the electrode and the wicking element. Any other suitable configurations and/or elements of the assembly are contemplated here as appreciated by those having ordinary skill in the art in view of this disclosure.

BRIEF DESCRIPTION OF THE DRAWINGS

Aspects of the present disclosure can be better understood with reference to the following drawings. Components of the drawing are not necessarily to scale, emphasis instead being placed upon clearly illustrating the principles of the present disclosure. Moreover, like reference numerals designate corresponding parts throughout the several views.

FIG. 26 is a plan view of the top of the embodiment of FIG. 23, showing an embodiment of a probe cap sealed (e.g., with silicone) to the reservoir body, and shown including an embodiment of a grommet seal disposed therein (e.g., and sealed with silicone), the grommet seal shown configured to allow an electrode wire to pass through.

FIG. 31 is a perspective view of the reservoir cap of FIG. 30, showing grommet seal pulled out of the reservoir cap and the electrode wire passing there-through.

FIG. 57 is a plan view from the underside of the reservoir body of FIG. 55, showing the teeth extending at least partially radially inward of a wick hole in the reservoir.

FIG. 58 is a perspective view of the wick retainer and the reservoir body shown in FIG. 55, the wick retainer being shown removed from the reservoir body.

FIG. 59 is a perspective view of the wick retainer of FIG. 58.

FIG. 60 is a side elevation view of the wick retainer of FIG. 59.

FIG. 61 is a perspective view of an inside of the reservoir body of FIG. 58, shown having the wick retainer removed.

FIG. 62 is a plan view from the top of the reservoir body of FIG. 61.

DETAILED DESCRIPTION

Figure 1:
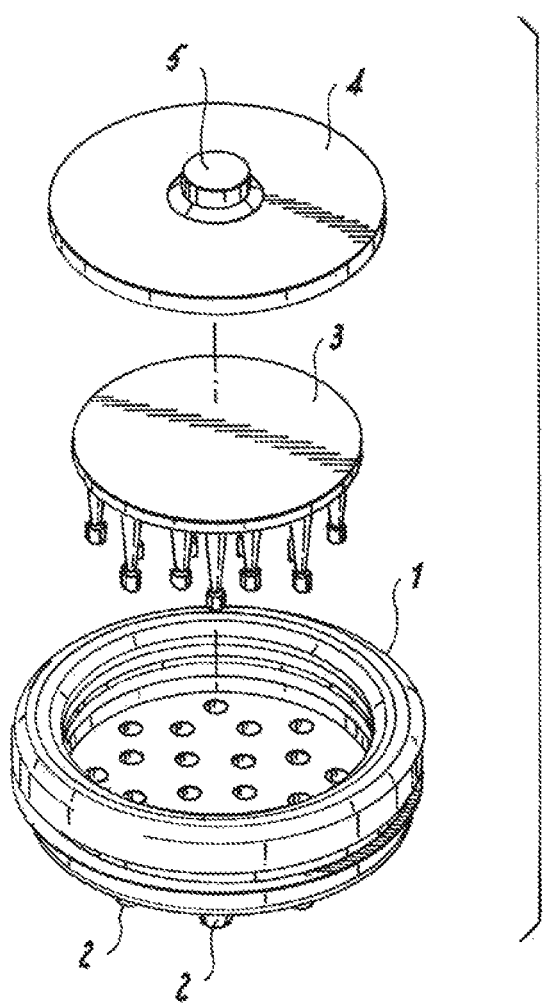
FIG. 1 depicts an electrode assembly designed to be placed on the scalp in areas normally covered with hair according to an embodiment of this disclosure.

As used in the specification and claims, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, the terms "comprises," "comprising," "containing," "having," and the like can have the meaning ascribed to them under U.S. patent law and can mean "includes," "including," and the like.

A "health care professional" shall be understood to mean any person providing medical care to a patient. Such persons include, but are not limited to, medical doctors, physician's assistants, nurse practitioners (e.g. an Advanced Registered Nurse Practitioner (ARNP)), nurses, residents, interns, medical students, or the like. Although various licensure requirements may apply to one or more of the occupations listed above in various jurisdictions, the term health care provider is unencumbered for the purposes of this patent application.

Unless specifically stated or obvious from context, the term "or," as used herein, is understood to be inclusive.

A "subject" shall be understood to include any mammal including, but not limited to, humans.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

The diagnosis of brain disorders is aided by many technologies such as magnetic resonance imaging (MRI), computerized axial tomography (CT scan), functional MRI (fMRI), positron emission tomography (PET) and magnetoencephalography (MEG). MRI and CT scan provide images of brain structure, PET images brain metabolism or blood flow, and MEG images neuronal function. However, none of these methods can be done at the bedside, due the size of the instruments or the need for special environments.

The EEG is the test of choice for evaluating patients presenting with altered mental status because it is the only current diagnostic tool for evaluating brain function that provides direct information regarding brain neuronal function and can be performed at the bedside. For this reason, it is widely used as a portable diagnostic tool in urgent care and emergency settings as well as in a laboratory environment. However, the diagnostic use of the EEG is limited by the difficulty in applying the multiple sensing electrodes required in the proper anatomical locations on the scalp in a way that ensures excellent and secure electrical contact. The proper application of EEG electrodes is particularly difficult to achieve in areas of the scalp normally covered by hair. Thus, proper application of EEG electrodes for diagnostic purposes must be performed by highly trained electroneurodiagnostic technicians. Even under ideal conditions, such as in an EEG laboratory, proper application of the electrodes by a skilled technician requires approximately 20 minutes. Due to the limited availability of trained technicians and the cost of ensuring their availability around the clock, the use of EEG in emergency and urgent care environments is limited primarily to large tertiary care hospitals.

Aspects of the this disclosure provide an electrode assembly and an electrode cap assembly designed to enable rapid application of a set of EEG electrodes (typically 21 electrodes) in the proper anatomical location on the scalp in such a way as to achieve reliable low impedance electrical contact with the scalp. Using this device along with standard portable EEG recording devices, an EEG can be obtained anytime and anywhere (e.g., in emergency departments, emergency vehicles, and in other acute care settings) by individuals who are not trained electroneurodiagnostic technicians.

At least one embodiment of this disclosure provides a plurality of novel electrode assemblies (e.g., 21 in some embodiments) that are attached to a headpiece (e.g., an elastic cap, rigid helmet, hat, or other suitable headpiece) at specified locations (through a snap mechanism in a typical embodiment), conductive traces (typically metal wire conductors, conductive cloth or other conductive materials), and electrical connections used to connect the electrode set with an EEG recording device. The electrode includes a reservoir configured to be filled with a conductive electrolyte fluid (e.g., saline solution, an electrolyte gel, or any other suitable conductive substance), a wicking material designed to control the flow of conducting fluid, and a reservoir top constructed from conductive material (e.g. silver/silver chloride disk or conductive rubber). The reservoir has multiple contact probe extensions designed to protrude through the hair to the scalp. The wicking material is a spongy material (e.g., foam in a typical embodiment) that sits within the reservoir and has probe extensions that fit within the probes attached to the reservoir. The wick ensures that the conductive fluid is in continuous contact with the scalp, thus maintaining electrical contact between the scalp and the electrode assembly.

FIG. 1 depicts an embodiment of an electrode assembly designed to be placed on the scalp in areas normally covered with hair. It is also contemplated that the embodiment of FIG. 1 can be used with areas not having hair. FIG. 1 is an exploded view depicting the key components of the electrode assembly that includes a hollow reservoir 1 made of a compressible material. In a typical embodiment, this reservoir 1 is fabricated from a conductive elastomeric material.

The reservoir 1 is configured to contain conducting fluid, such as a saline solution, a conductive gel, or any other suitable fluid. The undersurface of the reservoir 1 includes a flat surface with multiple holes and hollow contact probes 2 that penetrate the hair, facilitating electrical contact with the scalp. These hollow contact probes 2 can be aligned with the holes in the undersurface of the reservoir, providing a continuous path for flow of an electrolyte fluid between the reservoir 1 and the contact probes 2. In some embodiments embodiment, each of the contact probes 2 is approximately 8 mm in length with an outside diameter of 3 mm and an inside diameter of 2 mm.

In some embodiments, the elastomeric material of the reservoir 1 is made of a rubber material which may be conductive or insulating. This material can be compressible such that compression by the elastic cap 12 against the reservoir 1 creates sufficient pressure within the reservoir 1 to cause the fluid to pass from the reservoir 1 through the probes 2 to the scalp. This maintains sufficient pressure to ensure that the tips of the wicking material 6 remain wet, thus maintaining electrical contact with the scalp. Also, the compressible material of the reservoir 1 provides more comfort to the subject or patient under a wider range of conditions. It is contemplated that reservoir 1 can be rigid and that the wicking material 6 can remain wet via capillary action.

The second component of the electrode assembly is a wicking module 3 made of a porous material, such as foam or felt. The wicking material serves to hold the conducting fluid within the reservoir and hollow contacts, restricting the free-flow of the fluid sufficiently to wet the surface of the scalp beneath the probe 2 while preventing emptying of the reservoir 1 through leakage. The wicking material is preformed to fit within the reservoir 1 and has probes 6 that extend into the hollow contact probes 2, extending approximately 3 mm past the end of the hollow probes 2.

The third component of the electrode assembly is a reservoir top 4. This top 4 is typically constructed from a conductive metal, such as metal (e.g., silver/silver chloride) or an elastomeric conductive material, such as that used for the reservoir. The top 4 seals the conducting fluid within the reservoir 1 and is in direct contact with the wicking material 3, facilitating electrical contact through the electrolyte solution. In the center of the upper surface of the top 4 is a mushroom-shaped extension 5, which snaps into an electrode cap assembly, or other device such as flexible strips, to attach each electrode to the cap assembly. The center of the mushroom top 5 is a self-sealing needle port, typically constructed of rubber, which allows the user to refill the electrolyte solution, if required.

Figure 2:
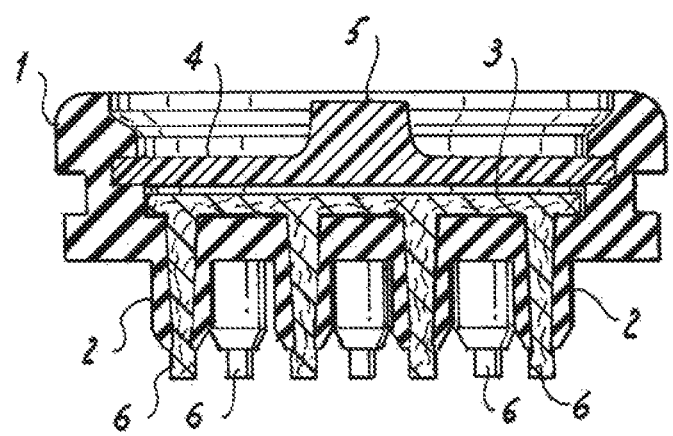
FIG. 2 depicts a side cross-sectional view of an electrode assembly according to an embodiment of this disclosure.

Referring now to FIG. 2, a side cross-sectional view of the hair electrode assembly illustrates how the wick probes 6 (which are part of the wicking module 3) extend from the reservoir 1 into and beyond the hollow contact probes 2 of the reservoir 1. FIG. 2 also illustrates that the reservoir top 5 can be recessed within reservoir 1.

Figure 3A:
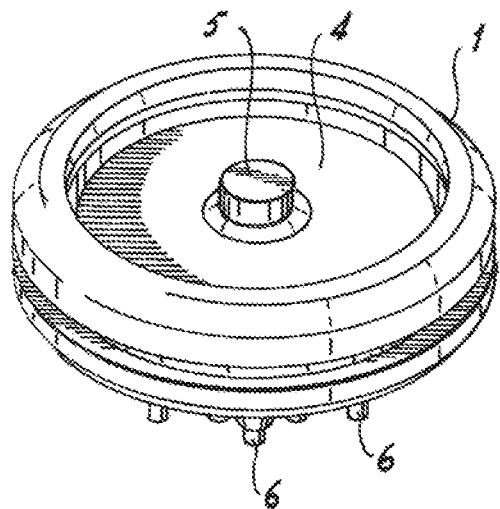
FIG. 3A provides a top view of the electrode assembly, illustrating the reservoir, the reservoir top, and the mushroom-shaped extension, which snaps into the electrode cap assembly forming an electrical contact with a trace embedded in the cap assembly according to an embodiment of this disclosure.

FIG. 3A provides a top view of the electrode assembly, illustrating the reservoir 1, the reservoir top 4, and the mushroom-shaped extension 5, which snaps into the electrode cap assembly forming an electrical contact with a trace embedded in the cap assembly.

Figure 3B:
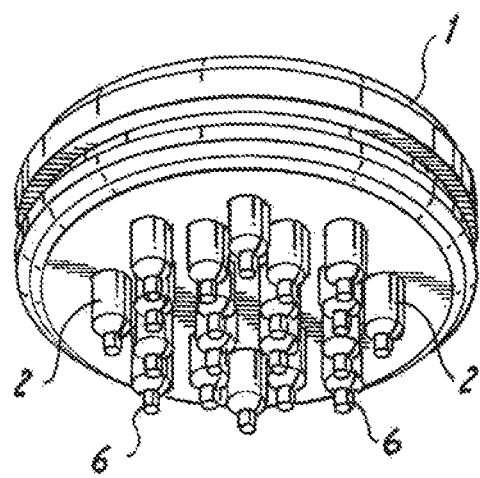
FIG. 3B illustrates the undersurface of the electrode assembly, demonstrating the undersurface of the reservoir, the hollow contact probes, and the tips of the wicking assembly that extend beyond hollow contact probes by approximately mm according to an embodiment of this disclosure.

FIG. 3B illustrates the undersurface of the electrode assembly, demonstrating the undersurface of the reservoir 1, the hollow contact probes 2, and the tips of the wicking assembly 6 that extend beyond hollow contact probes 2 by approximately 3 mm.

Figure 4:
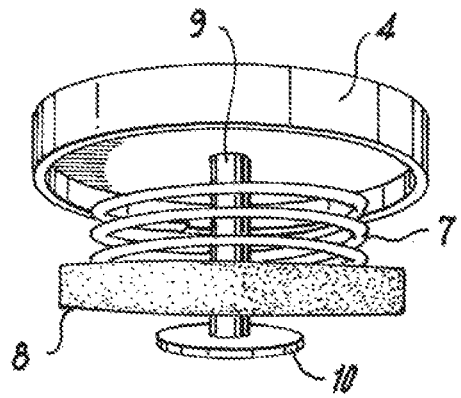
FIG. 4 illustrates an alternate embodiment of the disclosure wherein the electrode top is modified so as to include a spring made of plastic, metal or other suitable material according to an embodiment of this disclosure.

FIG. 4 illustrates an alternate embodiment of the disclosure wherein the electrode top 4 is modified so as to include a spring 7 made of plastic, metal or other suitable material. Below the spring 7 is an O-ring diaphragm 8, fabricated from rubber or other suitable material. These components are held in place by a shaft 9 made of metal or other electrical conducting material. A silver/silver chloride electrode 10 is attached to the inferior portion of the shaft 9. The spring 7 exerts pressure on the O-ring/diaphragm, which compresses the electrolyte fluid (e.g. normal saline) and the wicking material in the reservoir 1. Thus, as the fluid level declines in the reservoir 1 over time, the fluid passes from the reservoir 1 through the probes 2 to the scalp, the spring 7 pushes against the diaphragm 8 and the top 4, acting as a piston to maintain a steady pressure within the reservoir 1 to ensure that the tips of the wicking material 6 remain wet, thus maintaining electrical contact with the scalp.

In a third alternative embodiment, a hybrid reservoir configuration can be constructed from a non-compressible (e.g., hard rubber or plastic) material containing a spring assembly 7 and a O-ring diaphragm 8 as shown in FIG. 4 and discussed above. This material can constitute the upper ⅔ of the chamber. The lower ⅓ of the reservoir is composed of compressible elastomeric material as discussed above. This embodiment combines the adjustable pressure of the spring piston with the comfort and flexibility of the rubber chamber.

Figure 5A:
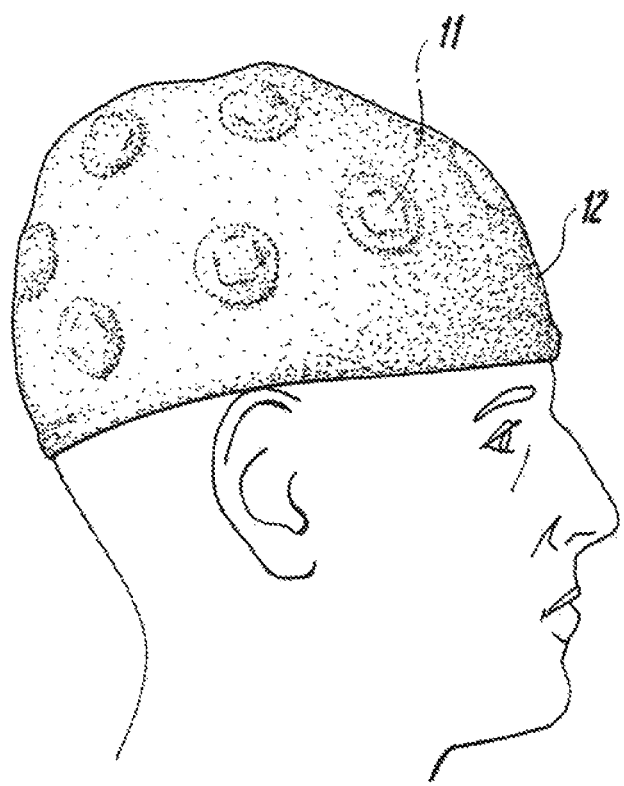
FIG. 5A illustrates a lateral view of an elastic cap assembly made from an elastic material such as spandex, which is sized to fit over a human head.
Figure 5B:
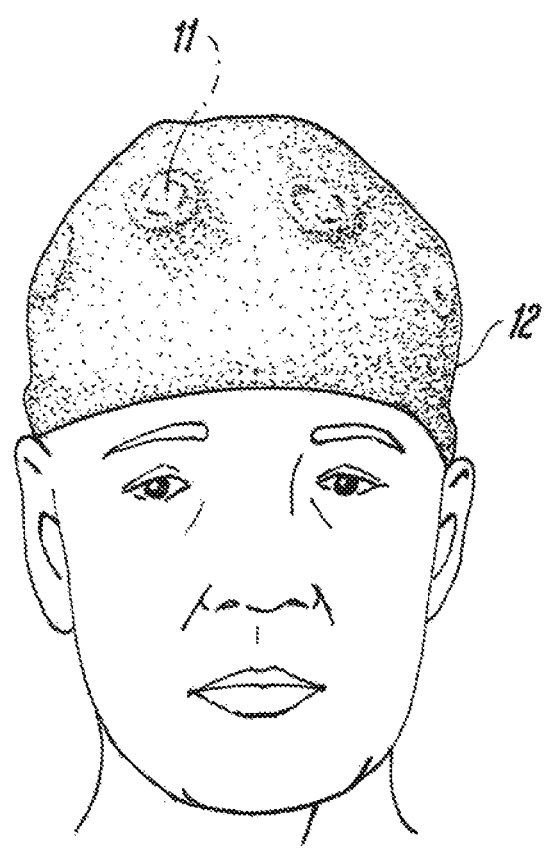
FIG. 5B provides a frontal view of the cap assembly according to an embodiment of this disclosure.

FIGS. 5A and 5B illustrate an elastic cap assembly made from an elastic material such as spandex, which is sized to fit over a human head. FIG. 5A provides a lateral view and FIG. 5B provides a frontal view of the cap assembly. The size of the cap varies, so as to be used for adults, children of various ages, and infants. A plurality of electrode assemblies 11 are attached to the undersurface of the cap, by snapping the mushroom shaped extension of each electrode assembly 5, as shown in FIGS. 6A, 6B, and 6C.

Figure 6A:
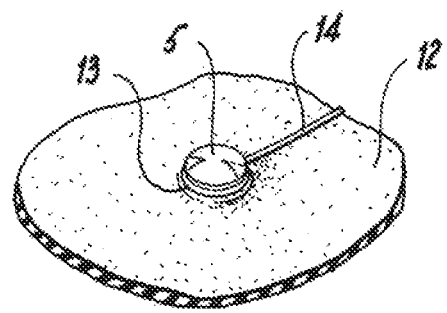
FIG. 6A shows a cutout of the exterior surface of the elastic cap illustrating the attachment of an example electrode assembly of FIG. 5A according to an embodiment of this disclosure.
Figure 6B:
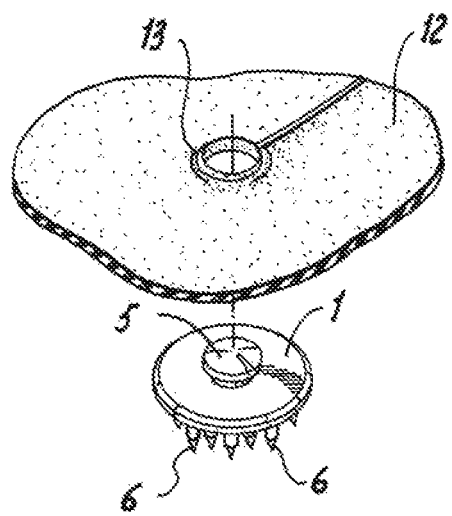
FIG. 6B illustrates the embodiment of FIG. 6A, showing the example electrode assembly removed therefrom.
Figure 6C:
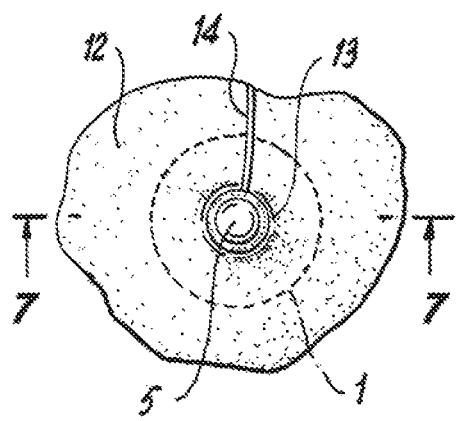
FIG. 6C illustrates a plan view of the embodiment of FIG. 6A.
Figure 11:
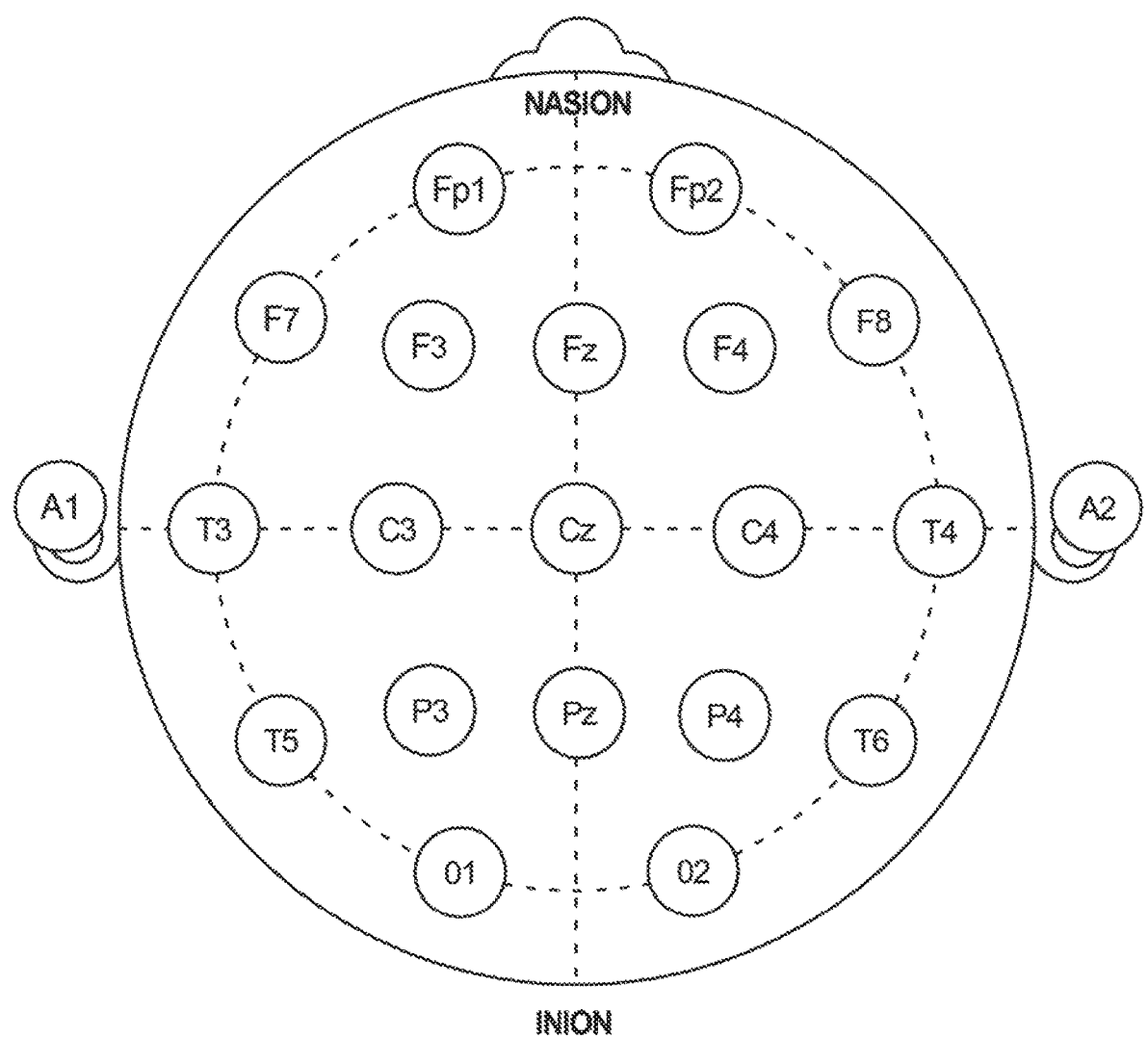
FIG. 11 depicts the location of electrodes in the International 10/20 System of electrode placement.

Electrode assemblies can attach to the electrode cap through snap mechanisms depicted in FIGS. 6A-6C, which can be attached to holes placed in the cap at specified distances. Any other suitable attachment is contemplated. The distances between holes in the cap are determined so that the electrode assemblies come into contact with the scalp at any suitable desired locations. In some embodiments, the inter-hole distances are set so that the electrode assemblies contact the scalp in anatomical locations approximating those of the International 10/20 System of electrode placement, which is depicted in FIG. 11. Typically, 21 electrodes are attached to the cap, so as to have 5 left parasagittal electrodes, 5 right parasagittal electrodes, 3 midline electrodes, 3 left temporal electrodes and 3 right temporal electrodes, as well as a ground and common reference electrode. The cap can be modified to include additional electrodes (typically for research purposes) or to include fewer electrodes, as required for the specific clinical or research application.

FIGS. 6A-6C show a cutout of the exterior surface of the electrode cap 12 illustrating the attachment of an example electrode assembly 11. The mushroom-shaped extension of the electrode top 5 snaps into a ring-shaped receptacle 13, which is attached to holes in the cap. In a typical embodiment, the receptacle may be sewn into place on the cap. The receptacle ring is fabricated from a conductive material such as metal or a conductive elastomeric material and is attached to a conductive trace 14. The trace 14 may be a metal wire, conductive cloth or other suitable electrical conducting material. In one embodiment, the conductive trace is over-molded into the elastic cap. The conductive trace 14 from each electrode assembly continues to a multi-contact electrical connector which, in turn, is plugged into an EEG recording device. The configuration of the multi-contact connector can be modified to be compatible with any given recording device.

Figure 7:
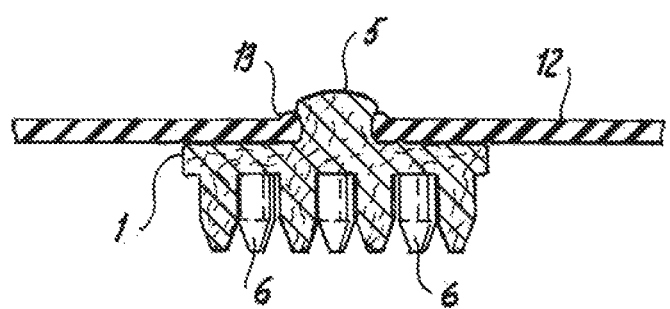
FIG. 7 is a side view of the electrode assembly and electrode top, illustrating how one of a plurality of electrode assemblies is attached to the undersurface of the elastic cap 12 in a typical embodiment of this disclosure according to an embodiment of this disclosure.

FIG. 7 is a side view of the electrode assembly and electrode top, illustrating how at least one of a plurality of electrode assemblies can be attached to the undersurface of the elastic cap 12 in at least one embodiment of this disclosure. The mushroom-shaped extension of the electrode top 5 protrudes through a hole in the elastic cap material and is fixed by snapping into the receptacle 13. As shown, the reservoir 1 can be located on the undersurface of the elastic cap.

Figure 8:
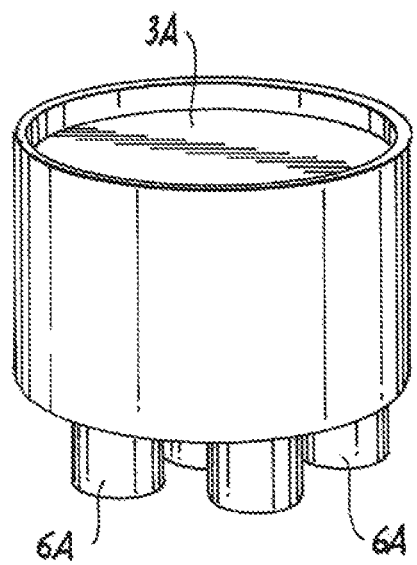
FIG. 8 depicts an alternate embodiment of this disclosure useful for electrodes that overlie scalp that is typically not covered with hair (e.g., Fp1, Fp2, F3, F4, F7, and F8 in the International 10/20 System of Electrode Placement) according to an embodiment of this disclosure.

The foregoing description illustrates some embodiments of an electrode configured to be used in areas of the scalp that are usually covered with hair, although it is contemplated that such embodiments can be used with areas of tissue not covered with hair. FIG. 8 depicts an alternate embodiment of this disclosure useful for electrodes that overlie scalp that is typically not covered with hair (e.g., Fp1, Fp2, F3, F4, F7, and F8 in the International 10/20 System of Electrode Placement), although it is contemplated that such embodiments can also be used in locations with hair. Such embodiments can include the three basic components discussed in the context of FIG. 1 (i.e., a hollow reservoir 1, wicking module 3, and reservoir top 4). However, the modified electrode would not include hollow contact probes 2 extending from the undersurface of the reservoir 1. This modification may be preferable in areas without hair because contact probe points are not required to establish contact through the hair. In such embodiments, the wicking material probes 6A would extend approximately 3 mm beyond the undersurface of the reservoir. Alternatively, the wicking material 3A may not have probes 6A, but there would be perforations in the underside of the reservoir 1 to allow the electrolyte to maintain contact with the scalp.

Figure 9:
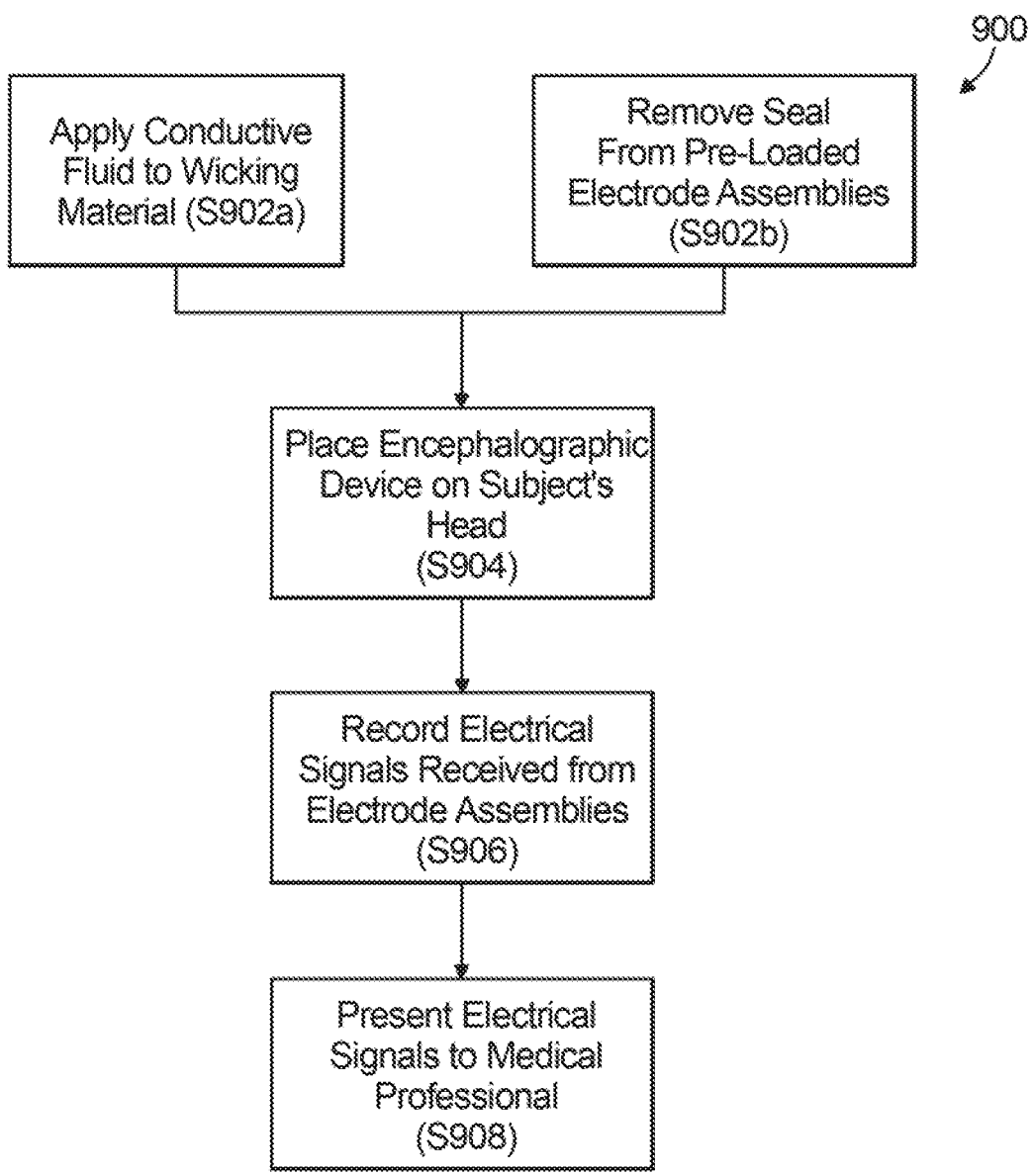
FIG. 9 depicts an encephalographic method 900 according to an embodiment of this disclosure.

Referring now to FIG. 9, another aspect of this disclosure provides an electroencephalographic method 900. In step S902a, a conductive fluid can optionally be applied to the electrode assemblies as discussed herein. In other embodiments, the electrode assemblies can be previously-loaded with conductive fluid. In some embodiments, the electrode assemblies are provided in sealed pouches that ensure sterility and minimize fluid loss from the electrode assemblies. Thus, in step S902b, a seal can be removed to allow fluid flow from a previously-loaded electrode assembly. In step S904, an encephalographic device is placed on the subject's head. The encephalographic device can be an encephalographic device as described herein. The encephalographic device can be marked in order to facilitate proper orientation of the encephalographic device with respect to the subject's head.

In step S906, electrical signals are received from the electrode assemblies and can be recorded (e.g., in computer readable media or on paper). After receiving the electrical signals, a recording and/or monitoring instrument can be configured to generate a visual tracing or other suitable display of the electrical signals from the various electrodes for interpretation by a user. In step S908, the electrical signals and/or the visual tracing (or other suitable display) are presented to a medical professional. The electrical signals can be presented to the medical professional in a variety of formats including in a paper report, in a computer readable file, on an electronic display, and the like.

Figure 10:
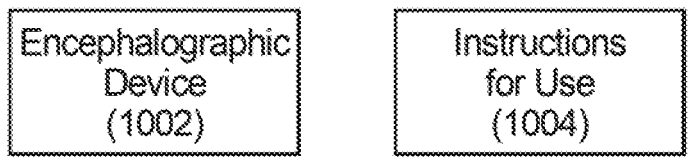
FIG. 10 depicts an electroencephalography kit including an electroencephalography device and instructions for use according to an embodiment of this disclosure.

Referring now to FIG. 10, another aspect of this disclosure provides an electroencephalography kit 1000 including an electroencephalography device 1002 and instructions for use 1004. The electroencephalography device 1002 can be an electroencephalography device as described herein. The instructions for use 1004 can be in written or electronic form and can include, for example, instructions on how to position the encephalographic device 1002 on the subject's head, how to couple the electroencephalography device 1002 to appropriate hardware for storing, displaying, and/or interpreting the electrical signals received from the electrode assemblies, general or specific instructions (e.g., word descriptions, illustrations, symbols) regarding methods of using the device, and collecting and measuring data.

Aspects of this disclosure can be particularly useful for detection and diagnosing concussions. For example, the electroencephalography kits can be stocked in ambulances for application while a patient is being transported to the hospital after a traffic accident. Likewise, the electroencephalography kits can be used by team doctors, trainers, and other medical professionals to quickly assess whether an athlete sustained a concussion in sports such as football, soccer, and hockey. In particular, embodiments of this disclosure can be worn under football or hockey helmets and automatically monitored via wireless communication to automatically detect concerning electrical signals.

Figure 12:
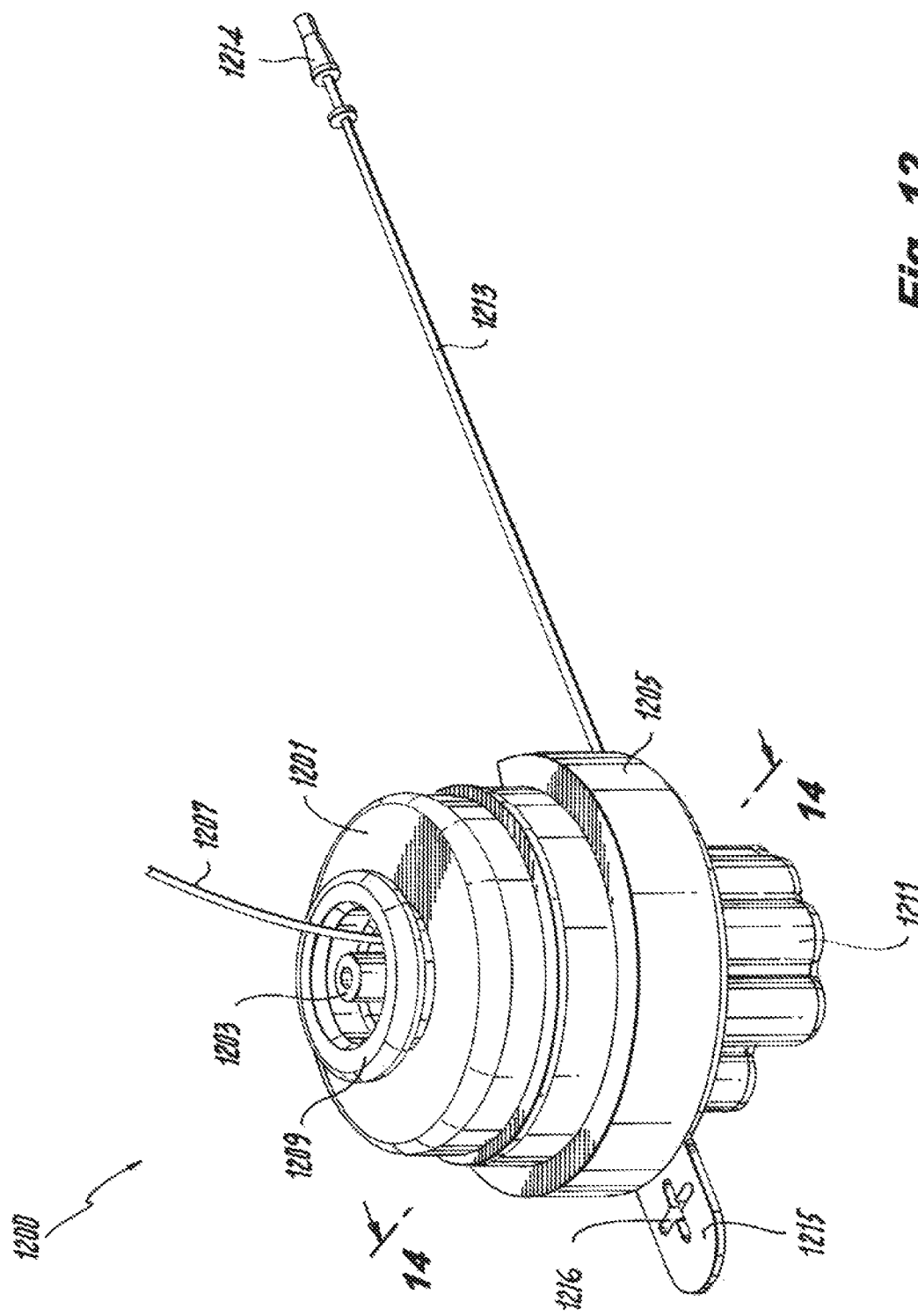
FIG. 12 is a perspective view of another embodiment of an electrode assembly in accordance with this disclosure.
Figure 13:
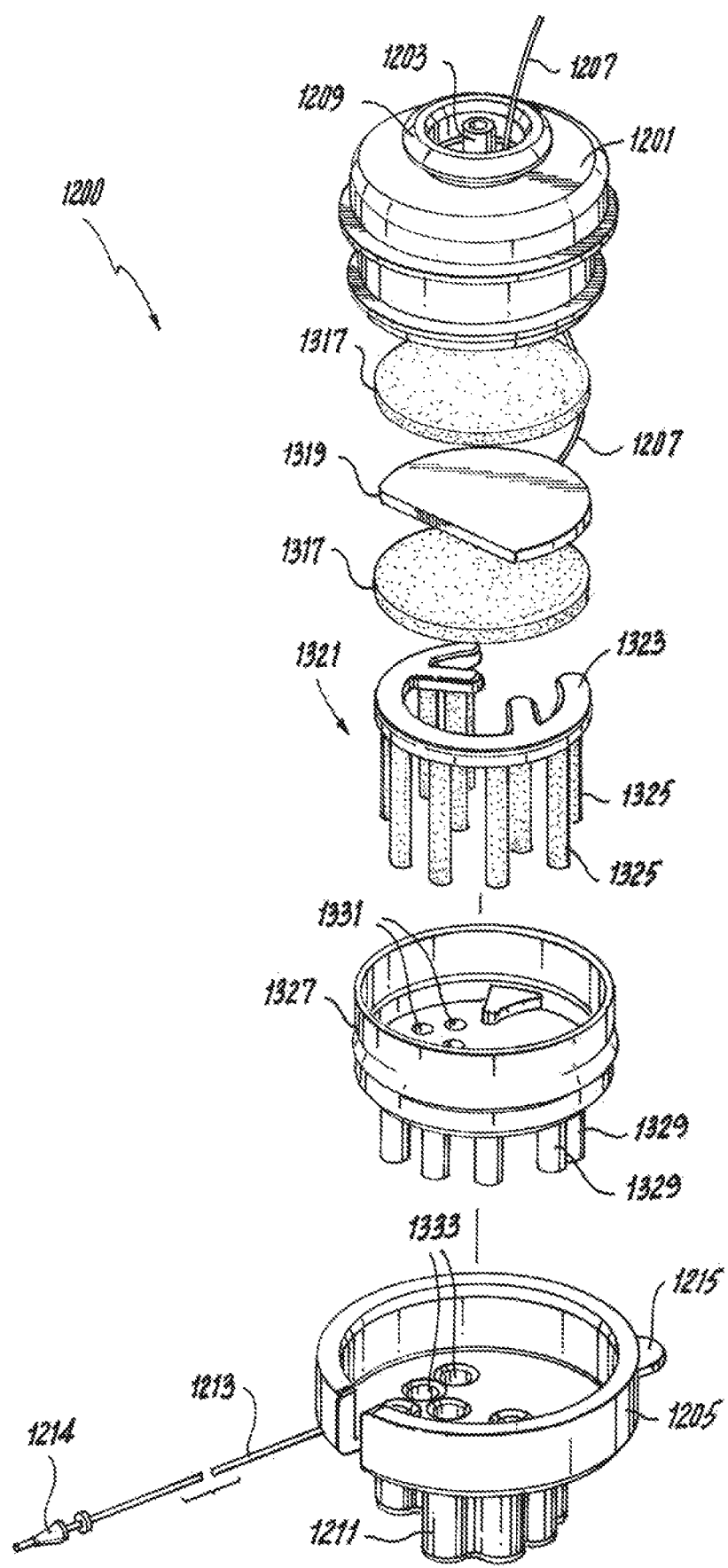
FIG. 13 is an exploded view the electrode assembly of FIG. 12.
Figure 14:
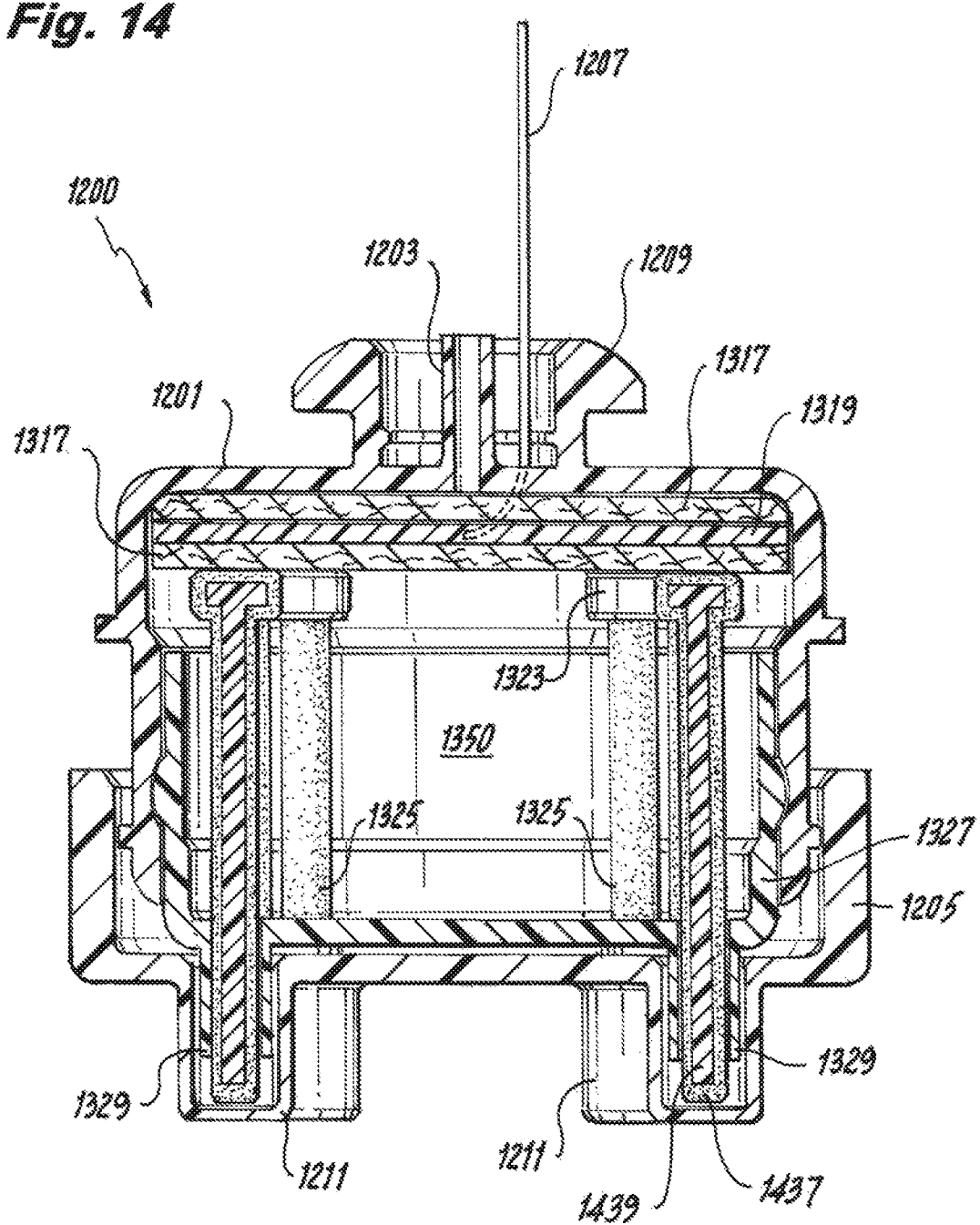
FIG. 14 is a cross-sectional view the electrode assembly of FIG. 12.

Referring to FIGS. 12-14, another embodiment of an electrode assembly 1200 is shown. Electrode assembly 1200 includes a reservoir cap 1201 that defines an interior cavity. A reservoir bottom 1327 is configured to be connected, moveably attached, and/or releasably attached to the reservoir cap 1201 in any suitable manner (e.g., bonding, bolting, molding, adhesives). The reservoir cap 1201 and the reservoir bottom 1327 define a reservoir 1350 that is configured to include at least one absorptive pad 1317, at least one electrode 1319, and at least a portion of a wicking element 1321.

The reservoir cap 1201 can be formed a substantially rigid material (e.g., polypropelene) or any other suitable material, including any suitable semi-rigid materials. The reservoir cap 1201 can define a fill port 1203 configured to be in fluid communication with the reservoir 1350. In some embodiments, the reservoir cap 1201 can also define and/or include an attachment portion (e.g., button attachment 1209) that is configured to allow the device to attach to a cap for a human head. The reservoir cap 1201 can also include a hole for one or more electrode wires 1207 and/or allow one or more electrode wires 1207 to exit through the fill port 1203.

The reservoir bottom 1327 can form and/or include one or more hollow contact probes 1329 extending therefrom which are in communication with holes 1331 define in the reservoir bottom. In some embodiments, the hollow contact probes 1329 are separate from the reservoir bottom 1327 and can be fixedly or removably attached and/or be interchangeable with different sets of hollow contact probes 1329. The hollow contact probes 1329 can be any suitable length, and may include differing lengths between one or more of the probes. In some embodiments, such as one intended for use with a portion of skin having hair, the hollow contact probes 1329 can be about 9 mm long. In some embodiments, such as one intended for use with a portion of skin not having hair, the hollow contact probes 1329 can be about 3 mm long.

The reservoir bottom 1327 can be made of any suitable rigid, semi-rigid, or flexible material (e.g., elastomeric plastic). If the reservoir bottom 1327 is configured to be semi rigid or flexible, the reservoir bottom 1327 can provide more comfort and flexibility for contact with skin at a test site (e.g., a scalp). It is also contemplated that the hollow contact probes 1329 can be made of a softer and/or more flexible material than the reservoir bottom 1327.

An electrode 1319 can be disposed within the reservoir 1350 and be connected to the one or more electrode wires 1207. As shown in FIGS. 13 and 14, the electrode can include any suitable shape that allows fluid to flow around a portion of the electrode 1319 such that the fluid can reach the bottom of the reservoir 1350. Also as shown in the embodiments of FIGS. 12-14, the electrode 1319 can be in contact (e.g., sandwiched between as shown) with one or more absorptive pads 1317. The electrode 1319 can be made of any suitable material (e.g., Silver-Silver-Chloride).

The absorptive pads 1317 can be any suitable absorptive material (e.g., a spongy material) that is configured to absorb a conductive fluid. The absorptive pads 1317 can be any suitable shape, thickness, and/or size and are not necessarily disk shaped as shown. The one or more absorptive pads 1317 can be configured to fill out any remaining interior space of the reservoir 1350.

The wicking element 1321 can include any suitable absorptive material similar to the absorptive pads. In some embodiments, the wicking element 1321 can include a rigid or semi-rigid frame 1439 having an absorptive layer 1437 disposed thereon. The absorptive layer 1437 can be deposited on the frame 1439 in any suitable manner (e.g., flocking).

The wicking element 1321 can include a base portion 1323 and one or more legs 1325 extending therefrom. The legs 1325 can be of any suitable length, shape, and/or width/diameter. In some embodiments, the frame 1439 of at least one of the legs 1325 can have a width of about 1 mm. The legs 1325 can be arranged in any suitable manner and/or form any suitable pattern or array. Disposing the legs 1325 in an array allows for simple manufacture and installation of the wicking element 1321 within the contact probes 1329.

The absorptive layer 1437 can be any suitable thickness (e.g., about 0.4) mm thick on at least a portion of the wicking element 1321. The legs 1325 are configured to enter into holes 1331 of the reservoir bottom 1327 and be contained in and/or protrude at least partially out of hollow contact probes 1329. In this respect, the legs 1325 are configured to contact the skin tissue of a patient and transmit electrical signals to the electrode 1319.

When assembled, the electrode assembly 1200 can be filled with a fluid through fill port 1203. The fluid can enter into the reservoir 1350 and be absorbed by the absorptive pads 1317. Through gravity and/or capillary action, the fluid within the pads and/or excess unabsorbed fluid can travel to the wicking element 1321 and be distributed into the absorptive layer 1437 and down throughout the legs 1325. In this respect, the legs 1325 stay wetted and allow for a continuous electrical connection to the electrode 1319.

In some embodiments, the electrode assembly 1200 can include a probe cover 1205 configured to overlay and/or seal the hollow contact probes 1329 to store the electrode assembly with fluid therein without allowing the wicking element 1321 to dry out. The probe cover 1205 can include sealed channels 1211 extending therefrom and holes 1333 for inserting the hollow contact probes 1329 into the sealed channels 1211. Each prober cover 1205 may include a daisy chain system including a shaft member 1213 having a male portion 1214 and a tab member 1215 having a female portion 1216. The male portion 1214 is configured to be inserted and locked to the female portion 1216 such that, when daisy chained, removing a first probe cap 1205 requires the removal of any daisy chained probe caps 1205.

Figure 15:
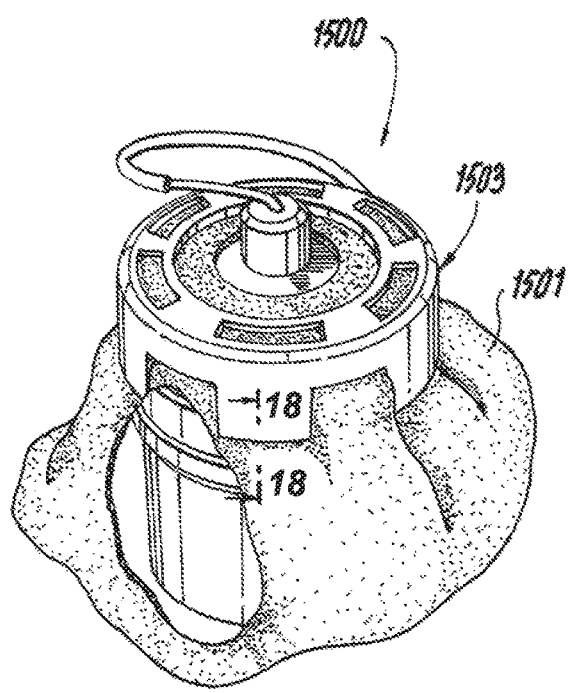
FIG. 15 is a perspective view of another embodiment of an electrode assembly in accordance with this disclosure (e.g., for positions on the head where there is hair), showing an embodiment of an electrode assembly clip attaching to the assembly to an elastic cap configured to fit a head.
Figure 16:
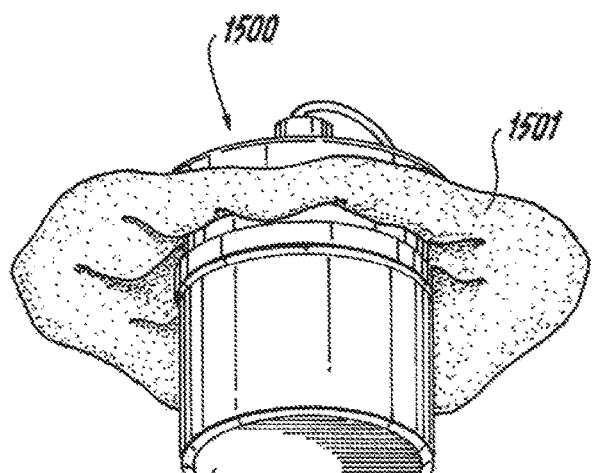
FIG. 16 is a perspective view of the embodiment of the assembly of FIG. 15, showing a portion extending from an underside of the elastic cap, wherein the portion is covered with a probe cover.
Figure 17:
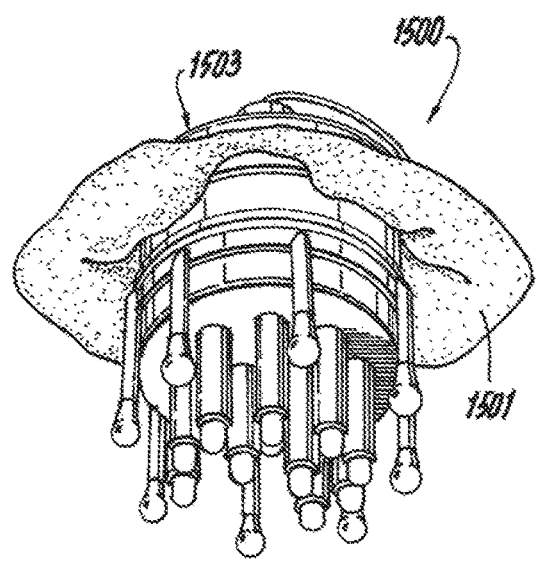
FIG. 17 is a perspective view of the embodiment of the assembly of FIG. 16, showing the probe cover removed.

Referring generally to FIGS. 15-62, a further embodiments and/or portions thereof are depicted. Referring to FIG. 15, a perspective view of another embodiment of an electrode assembly 1500 in accordance with this disclosure (e.g., for positions on the head where there is hair) is shown attached to an elastic cap 1501 (e.g., an elastic cap that fits on a user's head as described above) with an embodiment of an electrode assembly clip 1503. FIG. 16 is a perspective view of the embodiment of the assembly 1500, shown from an underside of the elastic cap 1501. The assembly 1500 can include a probe cover 1505 as shown in FIG. 16. FIG. 17 shows the probe cover 1505 removed.

Figure 18:
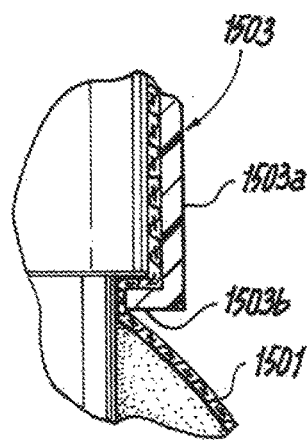
FIG. 18 is a partial cross-sectional schematic view of the embodiment of the electrode assembly clip shown in FIG. 15, showing the clip clipping the cap to the electrode assembly.
Figure 19:
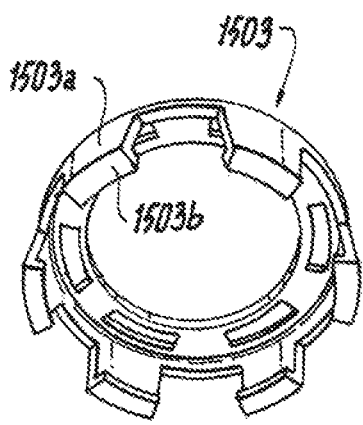
FIG. 19 is a perspective underside view of the clip of FIG. 18.
Figure 20:
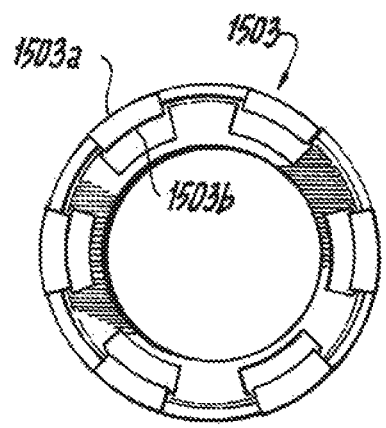
FIG. 20 is a plan view of the underside of the clip of FIG. 18.

Referring to FIGS. 18-20, the embodiment of the clip 1503 is shown. The clip 1503 can be made of hard plastic (e.g., polyethylene) or any other suitable material. As shown, the clip 1503 can include a plurality of clip arms 1503a. Each clip arm 1503a can include a clip tang 1503b that can include a tapered shape to slide over a ridge (e.g., a clip ridge as described below) to push the clip arms 1503a radially outward (or to deform the reservoir body), and to allow the arms 1503a to snap back radially inward after passing the ridge to allow clipping to the ridge.

Figure 21:
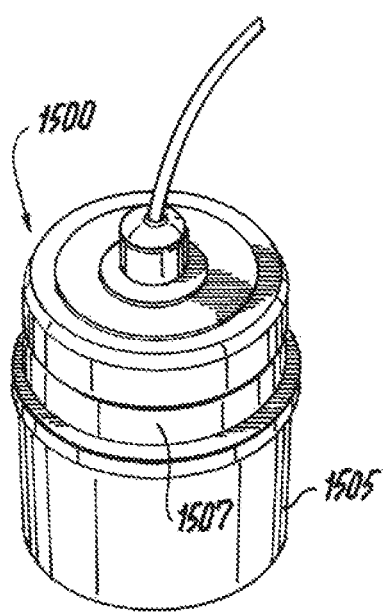
FIG. 21 is a perspective view of an embodiment of an electrode assembly, shown removed from the cap of FIG. 15, shown having a prove cover disposed thereon.
Figure 22:
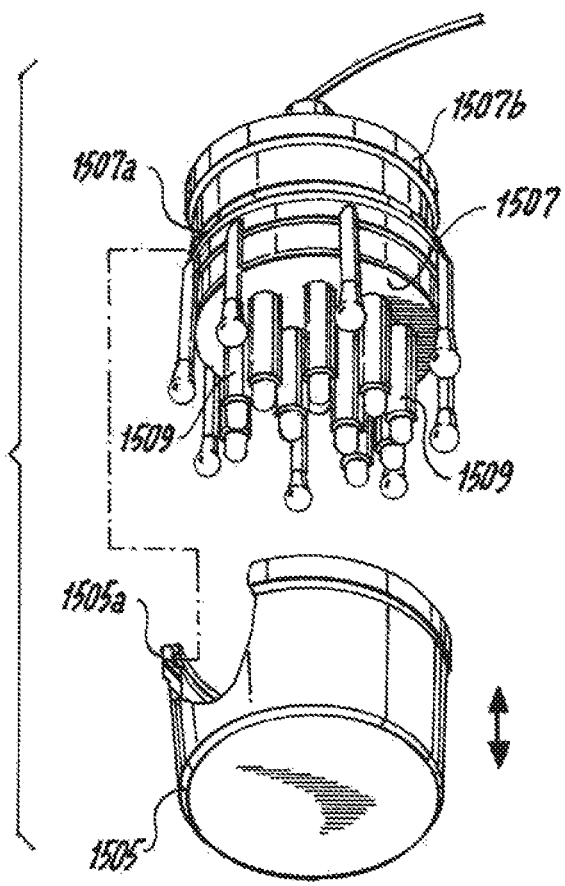
FIG. 22 is a perspective underside view of the embodiment of FIG. 21, shown having the probe cover removed and positioned to show probes extending from a reservoir body and a cavity defined by the probe cover which fits the probes therein, also showing a connecting interface between a ridge of the reservoir body and a pocket of the reservoir cap.
Figure 23:
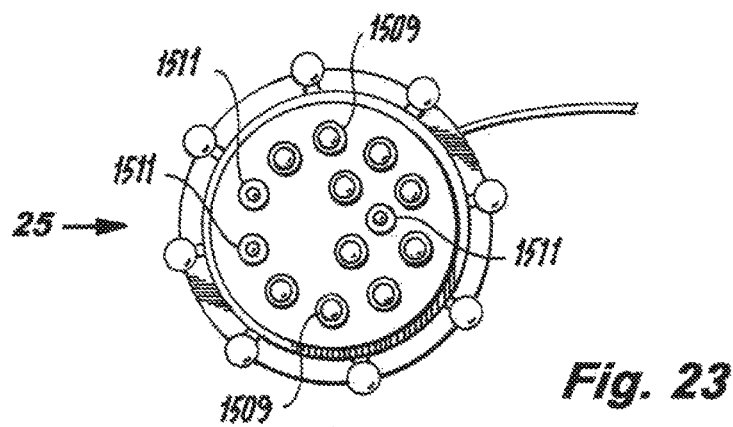
FIG. 23 is a plan view of the underside of the embodiment of FIG. 22, shown without the probe cover.
Figure 24:
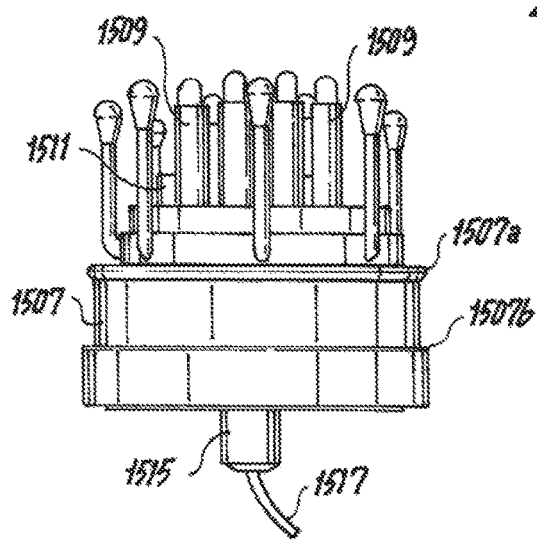
FIG. 24 is a side elevation view of the embodiment of FIG. 23.
Figure 25:
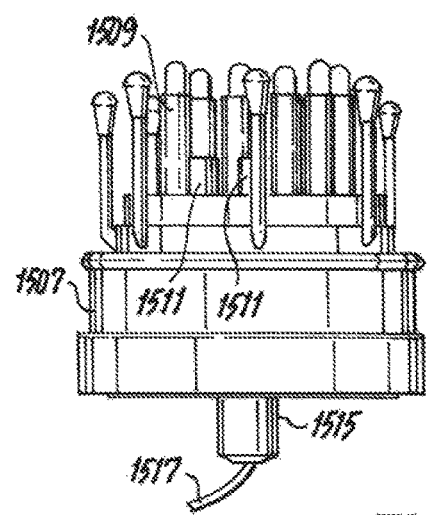
FIG. 25 is a side elevation view of the embodiment of FIG. 23, illustrating an about 90 degree view as in the embodiment of FIG. 24 illustrating short hollow contact probes.
Figure 26:
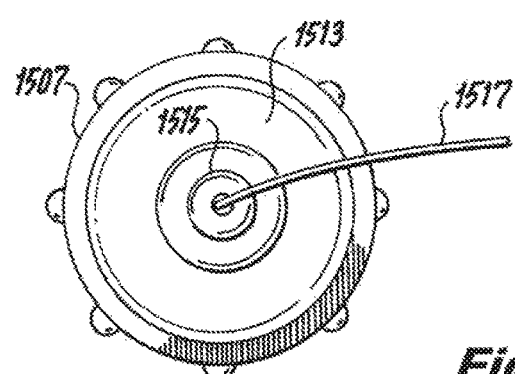
Figure 27:
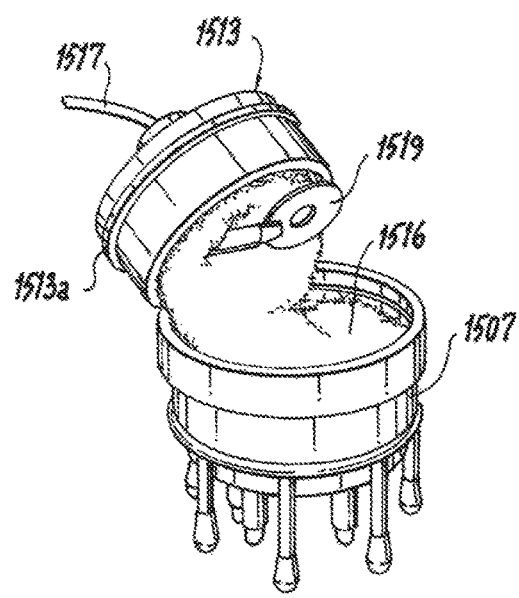
FIG. 27 is a perspective view of the embodiment of FIG. 23, shown having the probe cap removed from the reservoir body to reveal an interior thereof, and shown including an absorptive material (e.g., cotton) disposed therein.
Figure 28:
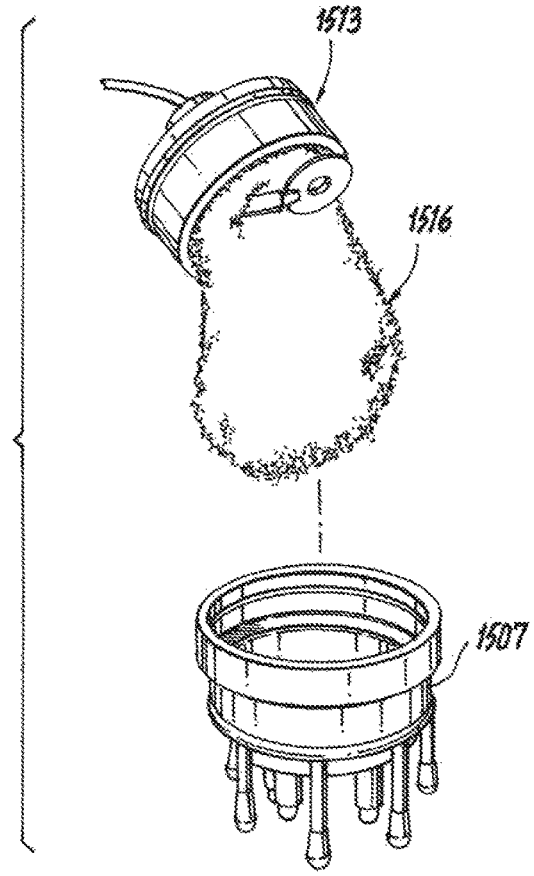
FIG. 28 is a plan view of the top of the reservoir body and an underside of the reservoir cap of FIG. 27, showing an embodiment of a disc electrode attached to the electrode wire and surrounded by the absorptive material.

Referring to FIG. 21, an embodiment of an electrode assembly 1500 is shown separated from the cap 1501 with the probe cover 1505 disposed thereon. In accordance with at least one aspect of this disclosure, an encephalographic electrode assembly 1500 can include a reservoir body 1507 defining at least a portion of a reservoir (e.g., a cavity defined within the assembly 1500 as described below). Referring to FIGS. 22-25, the assembly 1500 can include one or more hollow contact probes 1509 extending from the reservoir body 1507. The hollow contact probes 1509 can be integral with the reservoir body 1507 (e.g., made of a continuous molded flexible material). Each hollow contact probe 1509 can define a long leg channel therein that fluidly communicates with the reservoir.

The assembly 1500 also includes one or more short reservoir sleeves 1511 extending from the reservoir body 1507. Each short reservoir sleeve 1511 can define a short leg channel therein that fluidly communicates with the reservoir.

The reservoir body 1507 can further comprise a probe cover ridge 1507a defined on an outer surface of the reservoir body 1507. The probe cover ridge 1507a configured to mate with a pocket 1505a of a probe cover 1505 to retain the probe cover 1505 to the reservoir body 1509.

Also as shown, the reservoir body 1507 can include a clip ridge 1507b proximal the probe cover ridge 1507a and configured to allow a probe clip (e.g., clip 1503 as described above) to attach to the reservoir body 1507 to retain the assembly 1500 to an elastic cap 1501, e.g., as shown in FIGS. 15-17.

Referring to FIGS. 26-31, the assembly 1500 can further include a reservoir cap 1513 sealed (e.g., by contact and/or by one or more sealants, e.g., silicone) to the reservoir body 1507 to enclose and/or partially define the reservoir. In certain embodiments, the reservoir cap 1513 can be made of hard plastic (e.g., polyethylene) as shown, or any other suitable material. The reservoir body 1507 and hollow contact probes 1509/short reservoir sleeves 1511 can made of an elastic flexible material (e.g., silicone). The reservoir cap 1513 can include a lip 1513a configured to seat in the reservoir body 1507 on a corresponding inner ridge to prevent further insertion of the reservoir cap 1513 into the reservoir body 1507.

Figure 31:
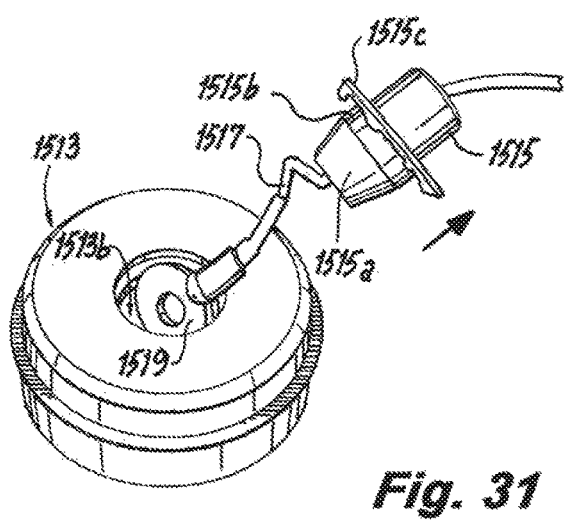

As shown, e.g., in FIG. 31, the assembly 1500 can include a grommet seal 1515 disposed in the reservoir cap 1513 (e.g., through a hole 1513b defined therein) and configured to allow an electrode wire 1517 to pass through the grommet seal 1515 to electrically connect to an electrode 1519 within the reservoir (e.g., as defined by the reservoir body 1507 and reservoir cap 1513. The grommet seal 1515 can be made of an elastic material (e.g., silicone), or any other suitable type of material.

As shown, the grommet seal 1515 can include a conical tip 1515a and a groove 1515b configured to be inserted through a hole 1513b in the reservoir cap 1513. In certain embodiments, the grommet seal 1515 can include a flange 1515c that abuts the reservoir cap 1513 (e.g., and can be sealed to the cap 1513 with a sealant, e.g., silicone).

In certain embodiments, the assembly 1500 can include an absorptive material 1516 (e.g., for holding electrolyte fluid, e.g., saline) disposed within the reservoir (e.g., defined by the reservoir body 1507 and the reservoir cap 1513) and in contact with the electrode 1519 and the wicking element (e.g., as described below). It is contemplated that the reservoir need not have an absorptive material 1516 and can be filled with electrolyte fluid.

Figure 29:
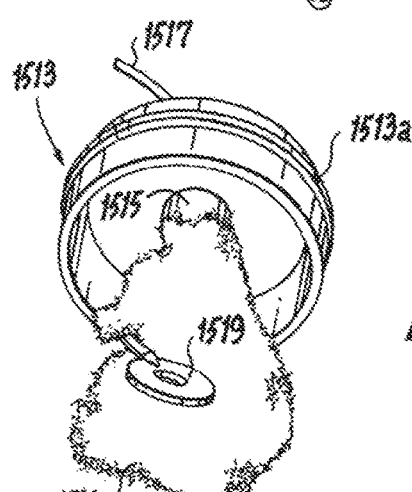
FIG. 29 is a perspective view of the reservoir cap of FIG. 28, showing the absorptive material pulled out, but attached (e.g., glued) to an underside of the grommet seal.
Figure 30:
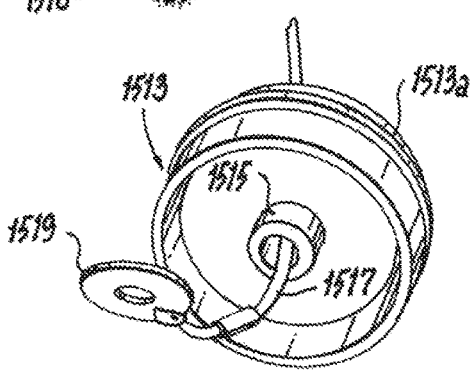
FIG. 30 is a perspective view of the reservoir cap of FIG. 29, showing the absorptive material removed, which shows the underside of the grommet seal extending through the reservoir cap and the electrode wire entering into the grommet seal.

In certain embodiments, the absorptive material 1516 can be unwoven cotton (such as a cotton ball). Any other suitable material is contemplated herein (e.g., woven fabric, a sponge). In certain embodiments, as shown in FIG. 29, the absorptive material 1516 can be bonded (e.g., with an adhesive or nay other suitable means) to the grommet seal 1515 (e.g., to the conical tip 1515a within the reservoir).

Figure 32:
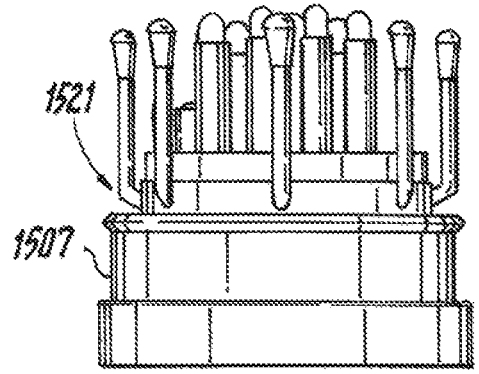
FIG. 32 is side elevation view of the embodiment of a reservoir body of FIG. 26, showing an embodiment of a stabilizer attached thereto.
Figure 34:
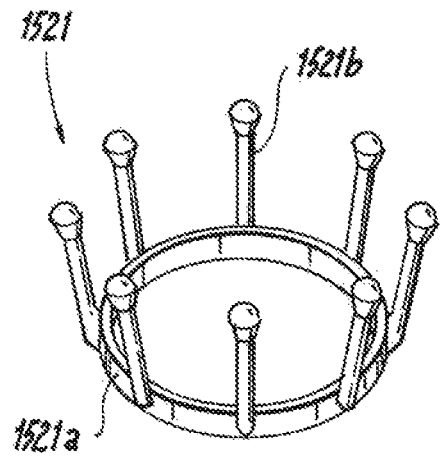
FIG. 34 is a perspective view of the stabilizer shown in FIG. 33.
Figure 33:
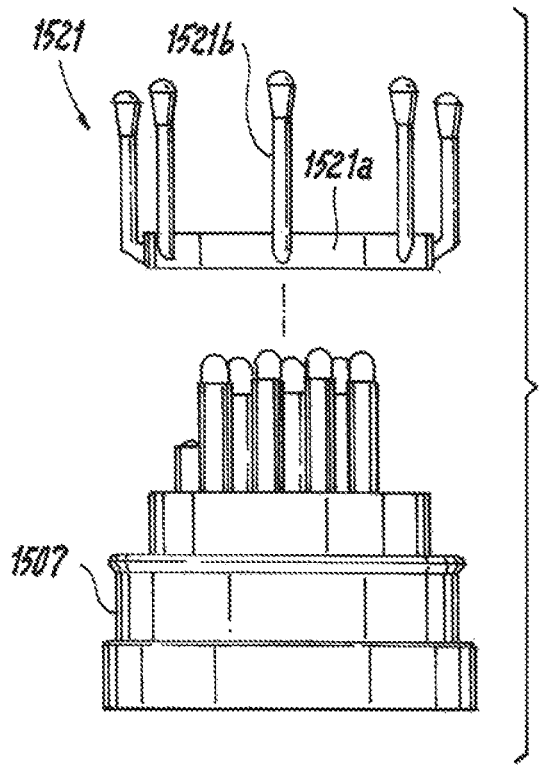
FIG. 33 is side elevation view of the embodiment of FIG. 32, showing the stabilizer removed from the reservoir body, and showing tips of long legs of a wicking element extending from hollow contact probes of the reservoir body.
Figure 35:
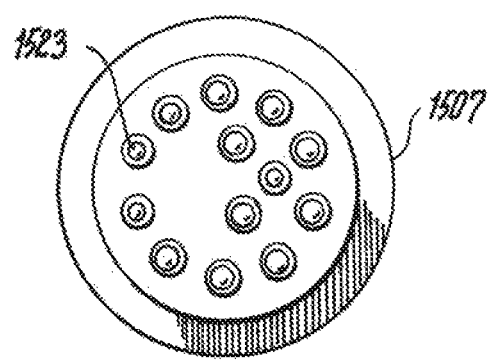
FIG. 35 is a plan view of an underside of the reservoir body of FIG. 32, showing the stabilizer removed.
Figure 36:
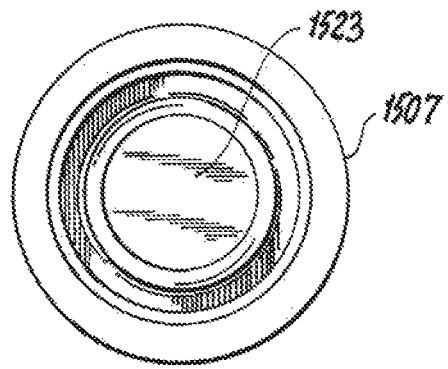
FIG. 36 is a plan view from the top of the reservoir body of FIG. 32, showing the absorptive material removed and having an embodiment of a wicking element disposed therein.
Figure 37:
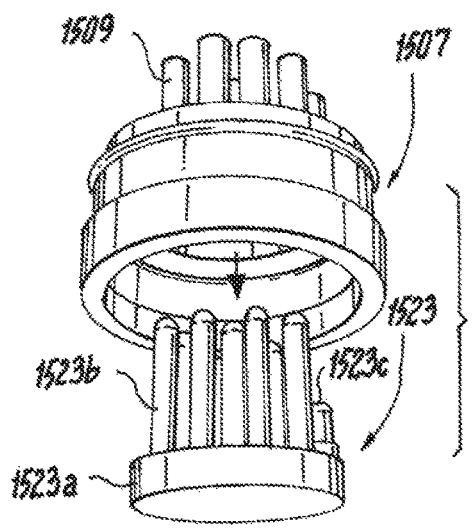
FIG. 37 is a perspective view of the reservoir body of FIG. 32, showing the wicking element removed therefrom.
Figure 40:
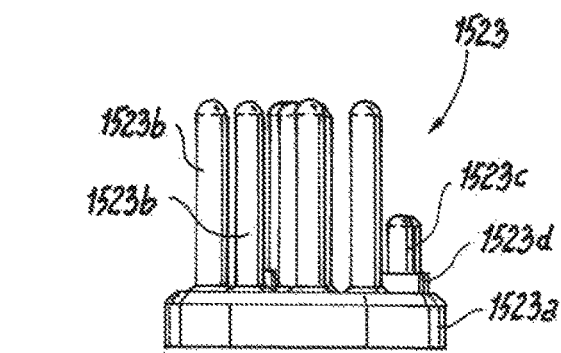
FIG. 40 is a side elevation view of the wicking element of FIG. 38.
Figure 38:
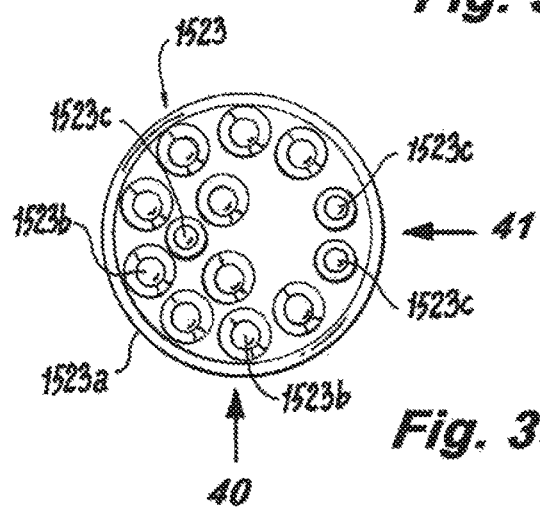
FIG. 38 is a plan view of the underside of the wicking element of FIG. 32, showing a layout of a plurality of legs of the wicking element.
Figure 41:
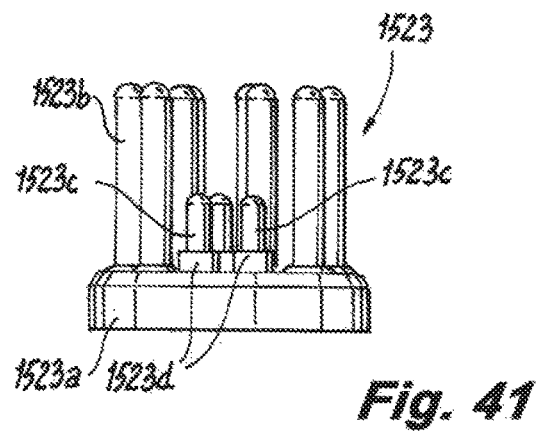
FIG. 41 is another side elevation view of the wicking element of FIG. 40, shown turned 90 degrees relative to the view of FIG. 40.
Figure 39:
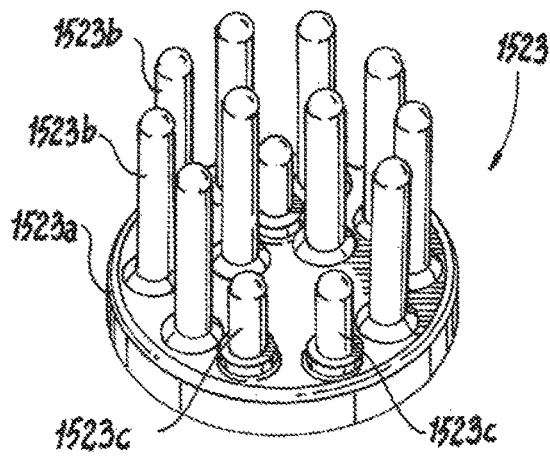
FIG. 39 is a perspective view of the wicking element of FIG. 38, showing a plurality of long legs and a plurality of short legs.

Referring to FIGS. 32-34, the assembly 1500 can include a stabilizer 1521 removably (or permanently) attached to the reservoir body 1507. In certain embodiments, the stabilizer 1521 can include a ring 1521a and a plurality of stabilizer legs 1521b radially outward of the hollow contact probes 1509 (and the reservoir sleeves 1511). The stabilizer legs 1521b extend from the ring 1521a (e.g., in a similar direction to the hollow contact probes 1509). The stabilizer 1521 can be made of hard plastic (e.g., polyethylene) or any other suitable material. The ring 1521 can be interference fit to the reservoir body 1507 (e.g., by having an inner diameter equal to or slightly less than the outer diameter of a lower portion of the reservoir body 1507).

In certain embodiments, the stabilizer legs 1521b can include rounded droplet tips as shown (e.g., to be atraumatic). Any other suitable tip is contemplated herein. In certain embodiments, the stabilizer legs 1521b can be angled to extend radially outward from the ring 1521a as well as distally. The stabilizer legs 1521b can include any suitable distal length (e.g., longer than the hollow contact probes 1509, but shorter than wicking element long legs as described below) and/or flexibility to allow the wicking element, e.g., as described below to contact skin, but to provide a more rigid, stabilizing force than the hollow contact probes 1509.

Referring to FIGS. 35-42, a wicking element 1523 can be disposed in the reservoir body 1507 in fluid communication with the reservoir (e.g., with the absorptive material 1516). The wicking element 1523 can include a wick body 1523a and one or more long legs 1523b that extend from the wick body 1523a and the insert into the one or more hollow contact probes 1509. The wicking element 1523 can also include one or more short legs 1523c which are shorter than the long legs 1523b and that extend from the wick body 1523a and insert into the one or more short reservoir sleeves 1511.

The wick body 1523a can include any suitable shape (e.g., a disk as shown, or shape as shown in the above described embodiments) of any suitable thickness and/or rigidity. For example, the wick body 1523a can be dimensioned to be substantially rigid and the long legs 1523b can be dimensioned to be semi-rigid and/or flexible.

In certain embodiments, the wicking element 1523 can be made of a single piece of material, e.g., by molding. For example, the wicking element 1523 can be made of material configured to absorb and wick fluid (e.g., saline) to tips of the long legs 1523b. In certain embodiments, the wicking element 1523 can be made of a solid porous plastic (e.g., molded ultra high molecular weight polyethylene). Any other suitable material and/or structural shape for the wicking element 1523 are contemplated herein. For example, the wicking element may be constructed from small diameter fibers and filaments made of polypropylene/polyethylene terephthalate (PET) or polyethylene (PE).

Figure 42:
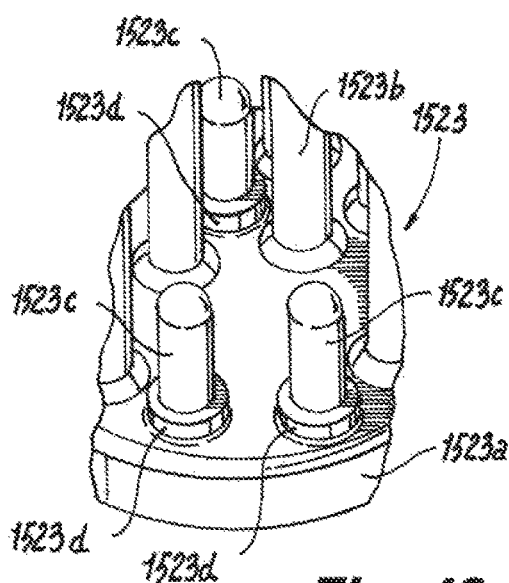
FIG. 42 is close up view of the wicking element of FIG. 38, showing a standoff lip at the base of each short leg.

As best illustrated in FIG. 42, the one or more short legs 1523c and/or the one or more long legs 1523b can include a standoff lip 1523d at a base of one or more of the short legs 1523c and/or long legs 1523b. In certain embodiments, as shown, each short leg 1523c can include a standoff lip 1523d at the base thereof.

While certain drawings show a beveled lip at the base of one or more long legs 1523b, it is contemplated that the long legs 1523b can meet the wick body 1523a without a lip at all (e.g., at a 90 degree angle), or such a lip can have any other suitable shape. While certain drawings show a beveled upper edge to the wick body 1523a, it is contemplated that the wick body 1523a may not have a beveled edge.

Figure 43:
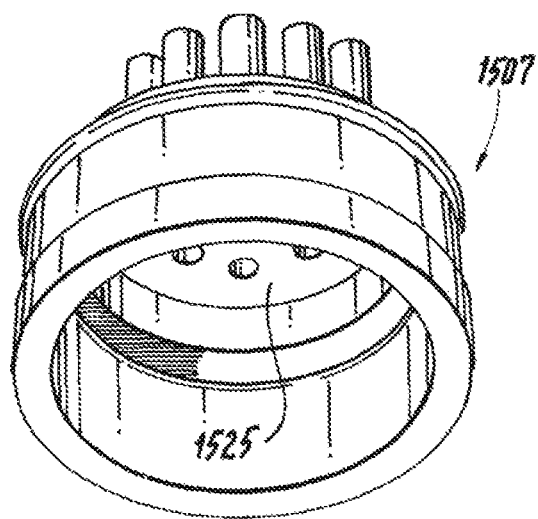
FIG. 43 is a perspective view of the reservoir body of FIG. 32, shown having the wicking element removed.
Figure 44:
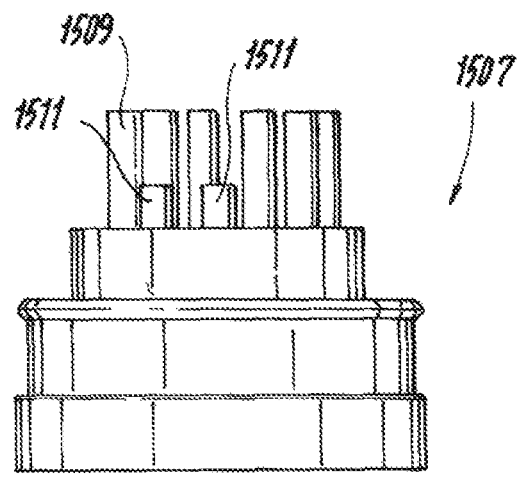
FIG. 44 is a side elevation view of the reservoir body of FIG. 43, showing short reservoir sleeves for the short legs of the wicking element to be received thereby (e.g., such that the short probes do not extend from the short reservoir sleeves).
Figure 45:
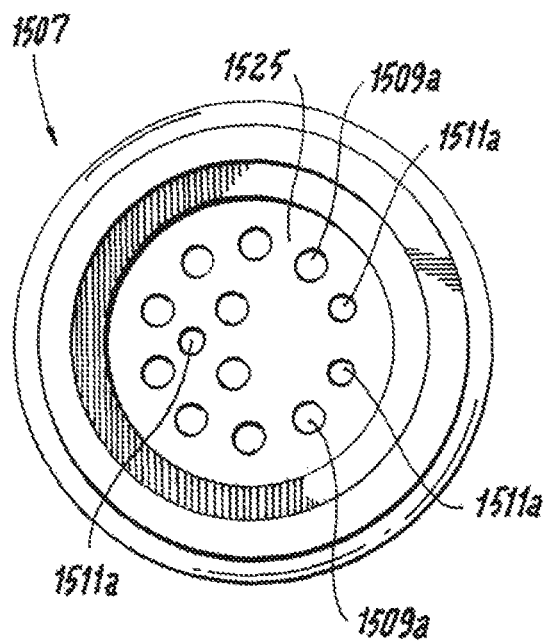
FIG. 45 is a plan view from the top of the reservoir body as shown in FIG. 44, showing a corresponding layout of openings to the contact probes/short reservoir sleeves for the legs of the wicking element to insert, and showing that a diameter of the short reservoir sleeves can be smaller than a diameter of the hollow contact probes.
Figure 46:
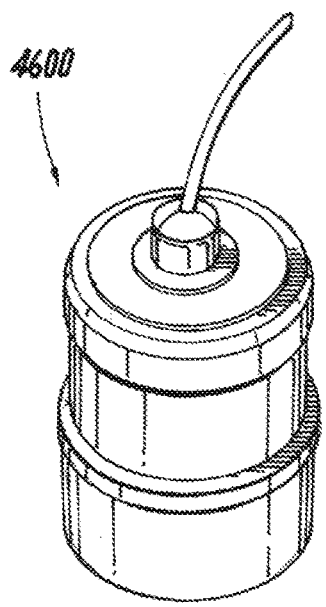
FIG. 46 shows a perspective exploded view of another embodiment of an electrode assembly in accordance with this disclosure (e.g., for positions on the head where there is little or no hair), shown removed from the elastic cap of FIG. 15 and showing a probe cover in partial cross-section clipping thereto.

Referring additionally to FIGS. 43-45, each standoff lip 1523d can be configured to provide a space between the reservoir body 1507 and the wick body 1523a within the reservoir when fully seated against an inner bottom surface 1525 of the reservoir body 1507. Such a space between the inner bottom surface 1525 of the reservoir body 1507 and the wick body 1523*a* can allow fluid to directly communicate with the long legs 1523*b* to improve wetting of the long legs 1523*b*. In certain embodiments, however, standoffs 1523*d* may not be present and the wick body 1523*a* can sit flush with the inner bottom surface 1525.

Each long leg 1523*b* can be dimensioned such that a tip of each long leg 1523*b* extends beyond a respective hollow contact probe 1509 when inserted therein. In certain embodiments, each short leg 1523*c* can be dimensioned to not extend beyond a respective short reservoir sleeve 1511 when inserted therein.

In certain embodiments, the short legs 1523*c* can be configured to prevent slide-out of the wicking element from the reservoir body 1507. For example, the one or more short legs 1523*c* can be larger, e.g., in outer diameter or other suitable dimension, than, e.g., the inner diameter or other suitable dimension, of the one or more short reservoir sleeves 1511 such that an interaction fit is created when the short legs 1523*c* are inserted into the short reservoir sleeves 1511. In certain embodiments, the one or more short legs 1523*c* can have the same width as the long legs 1523*b*. In such embodiments, the one or more short leg channels 1511*a* can have a smaller width (e.g., a smaller inner diameter or other suitable dimension) than the one or more long leg channels 1509*a*. In certain embodiments, the one or more long leg channels 1509*a* can be dimensioned to have the same or similar (e.g., plus or minus 10%) inner dimension as the outer dimension of the one or more long legs 1523*b* to provide a snug, sealed fit to prevent fluid from leaking around the long legs 1523*b*, but loose enough to not require a damaging sliding force to insert the long legs 1523*b*.

As shown, the one or more short legs 1523*c* can include at least three short legs 1523*c* positioned to form corners of a triangle (e.g., which can balance the force distribution of the short legs 1523*c* in preventing slide out of the wicking element 1523). Any other suitable number and/or position of short legs 1523*c* is contemplated herein. Embodiments prevent pushing the wicking element 1523 relative to the reservoir body 1507 under force of contact from being pressed against a scalp in use.

Referring to FIGS. 46-62 generally, another embodiment and/or portions thereof of an encephalographic electrode assembly 4600 are shown. Such an embodiment can be used for locations that do not have hair and only contact skin, for example. Embodiments of an elastic cap (e.g., as described above) can include two types of assemblies such as a plurality of assemblies 1500 (e.g., as hair electrodes) and a plurality of assemblies 4600 (e.g., as skin electrodes). In embodiments, embodiments for use on skin only are usually only positioned only forehead positions of the elastic cap (e.g., at Fp1, Fp2, F3, F4, F7, F8, and Fz).

Figure 48:
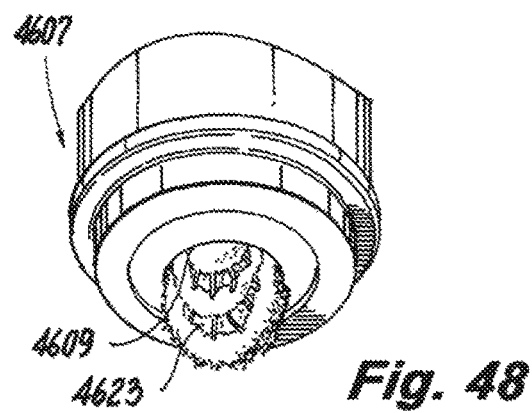
FIG. 48 is a perspective view from the underside of the assembly of FIG. 46, shown with the probe cover removed, and showing a wicking element extending therefrom.
Figure 49:
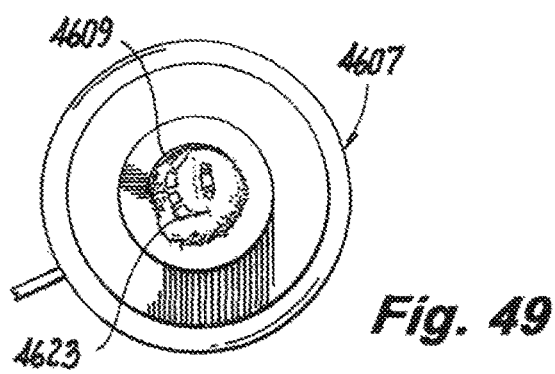
FIG. 49 is a plan view from the underside of the embodiment of FIG. 48.
Figure 47:
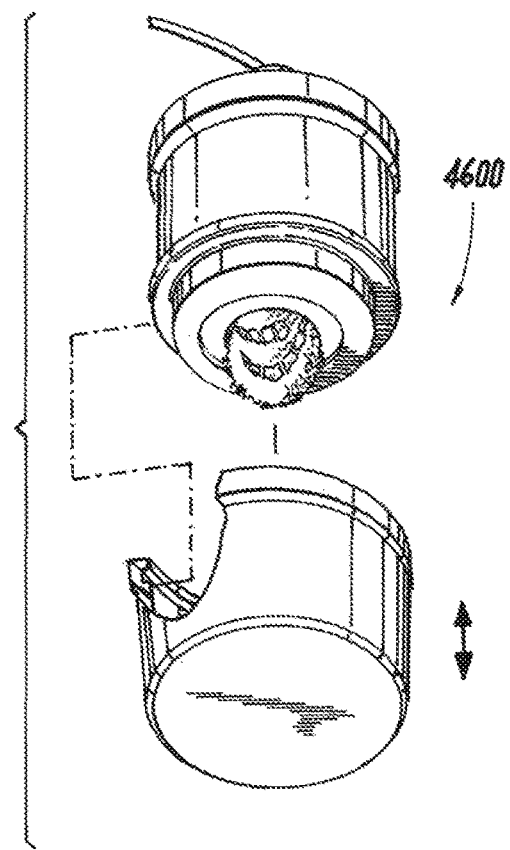
FIG. 47 is a perspective view of the embodiment of FIG. 46, shown next to a corresponding probe cover, also showing a connecting interface between a ridge of the reservoir body and a pocket of the reservoir cap.
Figure 50:
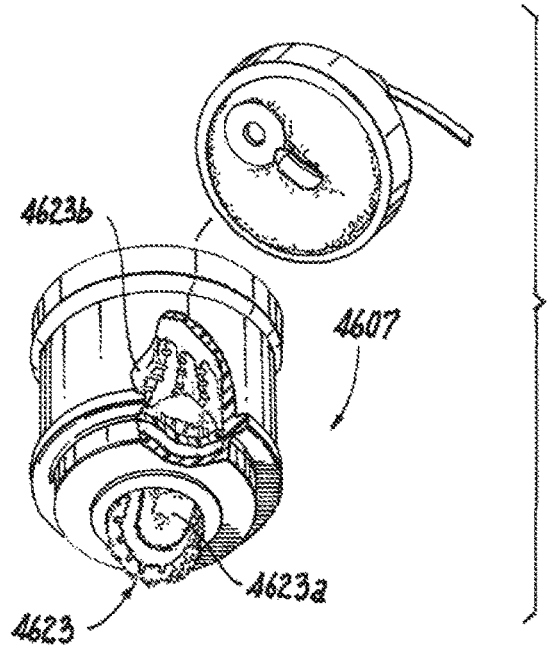
FIG. 50 is a plan view of the reservoir body removed from the reservoir cap of the embodiment of FIG. 46, showing a first absorptive material (e.g., a cotton ball material) in the reservoir cap, and the wicking material (e.g., a second absorptive material, e.g., a woven material) in the reservoir body.
Figure 51:
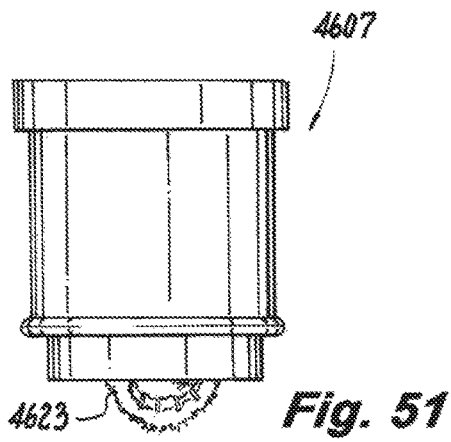
FIG. 51 shows a side view of the reservoir body of FIG. 50, showing the wicking element extending from the reservoir body.
Figure 54:
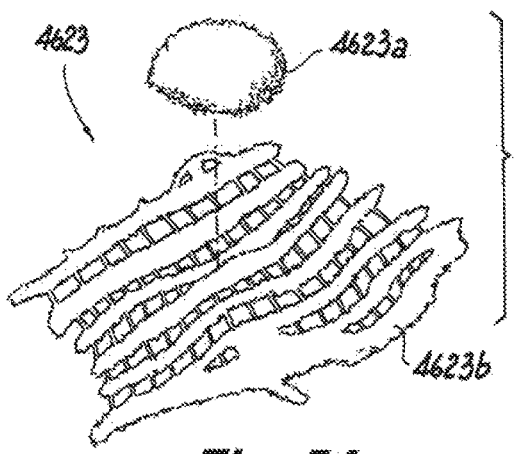
FIG. 54 is a perspective view of the wicking element of FIG. 53, shown disassembled.
Figure 52:
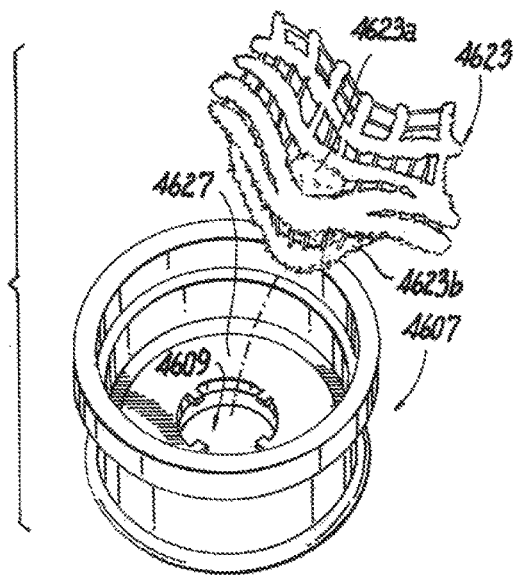
FIG. 52 is a plan view of the reservoir body of FIG. 51, showing the wicking material separated from the reservoir body, and showing a wicking element retainer disposed in the reservoir body.
Figure 55:
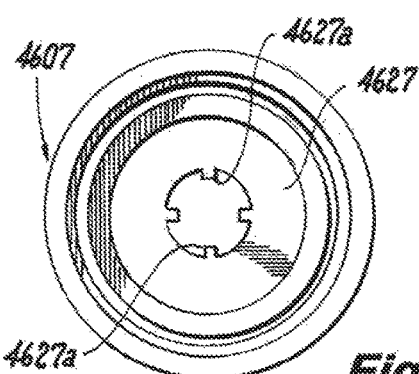
FIG. 55 is a close up view of the reservoir body of FIG. 52, showing teeth on an inner diameter of the wicking element retainer configured to interface with the woven absorptive material.
Figure 53:
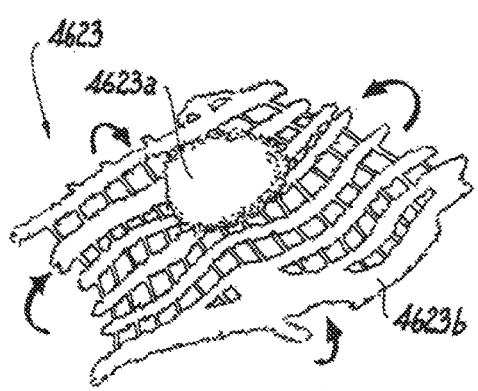
FIG. 53 is a perspective view of the wicking element of FIG. 52 shown unwrapped, showing a wad of denser absorptive material disposed in a woven absorptive material.
Figure 56:
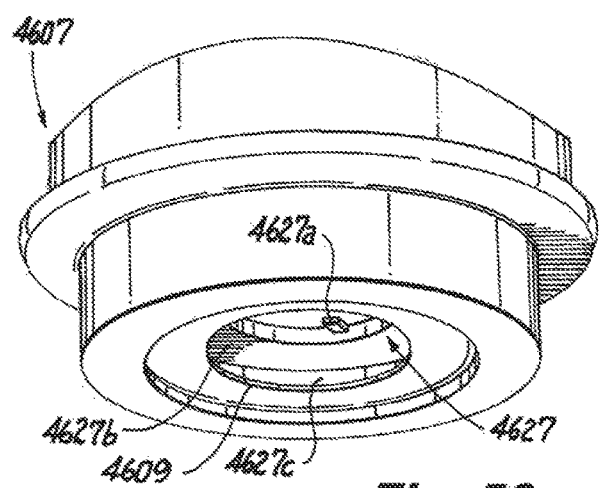
FIG. 56 is a perspective view from an underside of the reservoir body of FIG. 55, showing a space defined between reservoir body and an underside of the wicking element retainer.

Embodiments of electrode assembly 4600, e.g., as shown, can include portions that are the same or similar to one or more embodiments described above. However, the reservoir body 4607 does not include hollow contact probes 1509 or short sleeves 1511 extending therefrom. As shown in FIGS. 48 and 49, the reservoir body 4607 includes a large (e.g., single) opening 4609 having a wicking element 4623 extending therethrough. The wicking element 4623 can include a ball shaped tip that extends from the reservoir body 4607.

Referring to FIGS. 50-54, an embodiment of the structure of the wicking element 4623 can be seen. As shown, in certain embodiments, the wicking element 4623 can include a wad 4623*a* and a wrapping 4623*b*. The wad 4623*a* can include a ball shape and can be made of an unwoven material (e.g., a cotton ball material). The wrapping 4623*b* can be made of a woven material (e.g., cotton gauze). The wad 4623*a* can be wrapped in the wrapping 4623*b* and inserted through the opening 4609 to protrude from the reservoir body 4609, but to plug the opening such that the wicking element 4623 wicks fluid from the inside of the reservoir body 4607 in the reservoir.

Referring additionally to FIGS. 55-60, the assembly 4600 can include a retainer 4627. The retainer 4627 can be made of hard plastic (e.g., polyethylene) and/or any other suitable material.

The retainer 4627 can be configured to sit within the reservoir body 4607 and to grip the wicking element 4623 to prevent the wicking element 4623 from pushing back through the opening 4609 when pressed against a scalp and/or to prevent the wicking element 4623 from being pulled out of the reservoir body 4607. For example, the retainer 4627 can include a one or more teeth 4627*a* (e.g., four as shown) extending inwardly from a washer body 4627*b* and configured to grip the wrapping 4623*b* made of woven material such that the wrapping 4623*b* can be locked relative to the retainer 4627. After inserting the wrapping 4623*b* into the retainer 4627, the wrapping 4623*b* and/or the retainer 4627 can be twisted relative to the other to cause the teeth 4627*a* to grip into the wrapping 4623*b*. The wad 4623*a* can be larger than the inner diameter (or other suitable dimension) of the retainer 4627 and/or the teeth 4627*a* extending inwardly therefrom.

As best shown in FIGS. 58-60, the retainer 4627 can include a lip 4627*c* extending from the washer body 4627*b* (e.g., at an outer diameter thereof). The lip 4627*c* can be continuous or discontinuous. The lip 4627*c* creates a gap (e.g., as shown FIG. 56) between an inner bottom surface 4625 (e.g., as shown in FIGS. 61 and 62) and the retainer 4627. The gap can improve fluid contact with the wicking element 4623.

As disclosed herein, embodiments of the electrode assembly act as a fluid moving system that enables one to deliver a conductive electrolytic solution to the scalp through hair, so as to saturate the high impedance outer layer of the epidermis, thereby lowering impedances to levels that are acceptable for clinical diagnostic purposes. There should be an adequate flow of fluid to saturate the epidermal layer, but not an excessive flow of the fluid since too much flow can create recording problems and/or prematurely dry out the wicking material and the reservoir.

Any suitable combination(s) of any disclosed embodiments and/or any suitable portion(s) thereof are contemplated herein as appreciated by those having ordinary skill in the art. Any other suitable structural variations of any of the above disclosed embodiment is contemplated herein as would be appreciated by those having ordinary skill in the art in view of this disclosure.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

Although embodiments of this disclosure have been described using specific terms, such description is for illustrative purposes only, and it is to be understood that changes and variations may be made without departing from the spirit or scope of the following claims.

What is claimed is:

1. An assembly for use in encephalography, comprising:
a reservoir body defining at least a portion of a reservoir;
one or more hollow contact probes extending from the reservoir body, each defining a long leg channel therein that fluidly communicates with the reservoir;
one or more short reservoir sleeves extending from the reservoir body, each defining a short leg channel therein that fluidly communicates with the reservoir; and
a wicking element disposed in the reservoir body in fluid communication with the reservoir, the wicking element comprising:
a wick body;
one or more long legs extending from the wick body and inserted into the one or more hollow contact probes; and
one or more short legs, which are shorter than the long legs, extending from the wick body and inserted into the one or more short reservoir sleeves, wherein the short legs are configured to prevent slide-out of the wicking element from the reservoir body.

2. The assembly of claim 1, wherein the one or more short legs are larger than the one or more short reservoir sleeves such that an interaction fit is created when the short legs are inserted into the short reservoir sleeves.

3. The assembly of claim 2, wherein the one or more short legs have the same width as the long legs.

4. The assembly of claim 3, wherein the one or more short leg channels have a smaller width than the one or more long leg channels.

5. The assembly of claim 1, wherein the one or more short legs include at least three short legs positioned to form corners of a triangle.

6. The assembly of claim 1, wherein the one or more short legs or the one or more long legs include a standoff lip at a base of one or more of the short legs or long legs, each standoff lip configured to provide a space between the reservoir body and the wick body within the reservoir when fully seated against an inner bottom surface of the reservoir body.

7. The assembly of claim 6, wherein each short leg includes a standoff lip at the base thereof.

8. The assembly of claim 1, wherein each long leg is dimensioned such that a tip of each long leg extends beyond a respective hollow contact probe when inserted therein, and wherein each short leg is dimensioned to not extend beyond a respective short reservoir sleeve when inserted therein.

9. The assembly of claim 1, wherein the reservoir body further comprises a ridge defined on an outer surface thereof and configured to mate with a pocket of a probe cover to retain the probe cover thereto.

10. The assembly of claim 9, wherein the reservoir body includes a clip ridge proximal the probe cover ridge and configured to allow a probe clip to attach to the reservoir body to retain the assembly to an elastic cap.

11. The assembly of claim 1, further comprising a reservoir cap sealed to the reservoir body to enclose and/or partially define the reservoir.

12. The assembly of claim 11, wherein the reservoir cap is made of hard plastic, and the reservoir body and hollow contact probes are made of an elastic flexible material.

13. The assembly of claim 11, further comprising a grommet seal disposed in the reservoir cap and configured to allow an electrode wire to pass through the grommet seal to electrically connect to an electrode within the reservoir.

14. The assembly of claim 13, wherein the grommet seal is made of an elastic material.

15. The assembly of claim 14, wherein the grommet seal includes a conical tip and a groove configured to be inserted through a hole in the reservoir cap, wherein the grommet seal includes a flange that abuts the reservoir cap.

16. The assembly of claim 15, further comprising;
the electrode; and
an absorptive material disposed within the reservoir and in contact with the electrode and the wicking element.

17. The assembly of claim 1, further comprising a stabilizer removably attached to the reservoir body.

18. The assembly of claim 17, wherein the stabilizer includes a ring and a plurality of stabilizer legs radially outward of the hollow contact probes and extending from the ring.

19. The assembly of claim 18, wherein the stabilizer is made of hard plastic, wherein the ring is interference fit to the reservoir body, wherein the stabilizer legs include rounded droplet tips.

20. The assembly of claim 18, wherein the stabilizer legs are angled to extend radially outward from the ring.

* * * * *